United States Patent
Bird et al.

(12) 
(10) Patent No.: US 6,489,130 B1
(45) Date of Patent: Dec. 3, 2002

(54) DEATH ASSOCIATED KINASE CONTAINING ANKYRIN REPEATS (DAKAR)

(75) Inventors: Timothy A. Bird, Bainbridge Island, WA (US); G. Duke Virca, Bellevue, WA (US)

(73) Assignee: Immunex Corporation, Seattle, WA (US)

( * ) Notice: Subject to any disclaimer, the term of this patent is extended or adjusted under 35 U.S.C. 154(b) by 0 days.

(21) Appl. No.: 09/509,802

(22) PCT Filed: Aug. 4, 1999

(86) PCT No.: PCT/US99/17576
§ 371 (c)(1),
(2), (4) Date: Jun. 2, 2000

(87) PCT Pub. No.: WO00/08177
PCT Pub. Date: Feb. 17, 2000

Related U.S. Application Data

(60) Provisional application No. 60/095,269, filed on Aug. 4, 1998, provisional application No. 60/099,973, filed on Sep. 11, 1998, and provisional application No. 60/119,353, filed on Feb. 9, 1999.

(51) Int. Cl.[7] ............ G01N 33/53; C12P 21/04; C12N 9/00; C07K 1/00; C07H 21/02
(52) U.S. Cl. .................. 435/7.72; 435/7.1; 435/70.1; 435/183; 530/350; 536/23.1
(58) Field of Search .................. 435/7.1, 7.72, 435/70.1; 530/350; 536/23.1

(56) References Cited

U.S. PATENT DOCUMENTS 6,150,502 A * 11/2000 Strachan ............... 530/350

FOREIGN PATENT DOCUMENTS

| WO | WO-96/36730 A1 | * 11/1996 |
| WO | WO 99/04265 | 1/1999 |

OTHER PUBLICATIONS

Cohen et al., "DAP–kinase is a Ca2+/Calmodulin–dependent, cytoskeletal–associated protein kinase, with cell death–inducing functions that depend on its catalytic activity," EMBO Journal, 1997, vol. 16, No. 5, pp. 998–1008.*
Inbal, B., et al., "DAP Kinase Links the Control of Apoptosis to Metastasis," *Nature*, vol. 390, pp. 180–184 (1997).
Marra, M., et al., "The WashU–HHMI Mouse EST Project," EMBL Database Entry AI317448, Accession No. AI317448, XPoo2129808 (Dec. 18, 1998) Abstract.

* cited by examiner

*Primary Examiner*—John S. Brusca
*Assistant Examiner*—Young Kim
(74) *Attorney, Agent, or Firm*—Randolph N. Mohr; Suzanne A. Sprunger

(57) ABSTRACT

The invention is directed to purified and isolated novel DAKAR (death associated kinase containing ankyrin repeat) polypeptides, the nucleic acids encoding such polypeptides, processes for production of recombinant forms of such polypeptides, antibodies generated against these polypeptides, fragmented peptides derived from these polypeptides and the uses of the above.

12 Claims, 1 Drawing Sheet

```
CONSENSUS:      -G-TPLH-AA--GH---V--LL--GA--N--N-
                   (A)                      (D) (D)
DAKAR rpt 1  KGSTPLHMAVERKGRGIVELLLARKTSVNAKDE
DAKAR rpt 2  DQWTALHFAAQNGDEASTRLLLEKNASVNEVDF
DAKAR rpt 3  EGRTPMHVACQHGQENIVRTLLRRGVDVGLQGK
DAKAR rpt 4  DAWLPLHYAAWQGHLPIVKLLAKQPGVSVNAQT
DAKAR rpt 5  DGRTPLHLAAQRGHYRVARILIDLCSDVNICSL
DAKAR rpt 6  QAQTPLHVAAETGHTSTARLLLHRGAGKEALTS
DAKAR rpt 7  EGYTALHLAAQNGHLATVKLLIEEKADVMARGP
DAKAR rpt 8  LNQTALHLAAARGHSEVVEELVSADLIDLSDEQ
DAKAR rpt 9  QGLSALHLAAQGRHSQTVETLLKHGAHINLQSL
```

FIGURE 1

DEATH ASSOCIATED KINASE CONTAINING ANKYRIN REPEATS (DAKAR)

CROSS-REFERENCE TO RELATED APPLICATION

This application is a national application under 35 U.S.C. §371 of International Application No. PCT/US99/17576, having an international filing date of Aug. 4, 1999; which claims the benefit of provisional applications U.S. Ser. No. 60/095,269, filed Aug. 4, 1998, U.S. Ser. No. 60/099,973, filed Sep. 11, 1998, and U.S. Ser. No. 60/119,353, filed Feb. 9, 1999; all of which are incorporated by reference herein.

BACKGROUND OF THE INVENTION

1. Field of the Invention

The invention is directed to purified and isolated novel DAKAR (death-associated kinase containing ankyrin repeat) polypeptides and fragments thereof, the nucleic acids encoding such polypeptides, processes for production of recombinant forms of such polypeptides, antibodies generated against these polypeptides, fragmented peptides derived from these polypeptides, and uses thereof.

2. Description of Related Art

Cell death occurs by one of two mechanisms, necrosis or apoptosis. Necrosis is uncontrolled cell death which usually results from environmental stresses such as severe trauma to cells. Cell death from apoptosis, however, results from specific internal signals that activate a cell's death program. Therefore, apoptosis is termed programmed cell death.

The morphological changes that occur during apoptosis are characterized by DNA degradation by endonucleases, cytoplasmic and nuclear condensation, and the formation of membrane "blebs" or apoptotic bodies (T. G. Cotter et al., *Anticancer Res*, September–October: 10(5A):1153–9, 1990). Neighboring cells then move in to engulf the remaining cellular debris. Programmed cell death has been observed during early development and in immune responses where cells, such as lymphocytes, are eliminated via apoptosis when they are no longer needed (C. A. Janeway, Jr. and P. Travers, *Immuno Biology* G:3 (Garland Publishing Inc., 2nd ed. 1996)).

The biochemical mechanism driving apoptosis begins with a ligand/receptor induced signal that activates (in part through phosphorylation or dephosphorylation) other proteins, such as kinases, along the signal transduction pathway and ultimately concludes with the activation of the cell death program. Such ligand/receptor pairs that can induce apoptosis are, for example, TNF/TNF-RI, TNF/TNF-R2, CD95 ligand/CD95, TRAIL/TRAIL-R1, and TRAIL/TRAIL-R2.

Many of the receptors above and the intracellular kinases that play a role in transducing the signal from the membrane to the nucleus contain a stretch of 80 amino acids that is necessary to activate cell death. This "death domain" (DD) functions by interacting with other proteins via their DD or via self association. Over expression of many DD-containing proteins results in cell death, indicating that these proteins may play a role in apoptosis (K. Schulze-Osthoff et al., *Eur. J. Biochem*, 254:439–459, 1998).

Among the proteins involved in apoptosis are the eukaryotic protein kinases (e.g., cell death related kinases, cell proliferation related kinases, etc.). These kinases make up a large and rapidly expanding family of proteins related on the basis of homologous catalytic domains. Spurred by the development of gene cloning and sequencing methodologies, distinct protein kinase genes have been identified from a wide selection of invertebrates and lower eukaryotes, including Drosophila, *Caenorhabditis elegans*, Aplysia, Hydra, Dictyostelium, and budding (*Saccharomyces cerevisiae*) and fission (*Schizosaccharomyces pombe*) yeast. Homologous genes have also been identified in higher plants. Protein kinases, however, are not limited to the eukaryotes. Enzyme activities have been well documented in prokaryotes, but the prokaryotic protein kinase genes are not obviously homologous to those of the eukaryotes.

Given the important function of kinases in general and DAKAR specifically, there is a need in the art for additional members of the kinase family. There is also a need in the art for the identity and function of proteins having linase activities. Moreover, given the important roles kinases may play in apoptosis, there is an unmet need for therapeutic compounds which interfere with apoptosis.

In another aspect, the identification of the primary structure, or sequence, of an unknown protein is the culmination of an arduous process of experimentation. In order to identify an unknown protein, the investigator can rely upon a comparison of the unknown protein to known peptides using a variety of techniques known to those skilled in the art. For instance, proteins are routinely analyzed using techniques such as electrophoresis, sedimentation, chromatography, sequencing and mass spectrometry.

In particular, comparison of an unknown protein to polypeptides of known molecular weight allows a determination of the apparent molecular weight of the unknown protein (T. D. Brock and M. T. Madigan, *Biology of Microorganisms* 76–77 (Prentice Hall, 6d ed. 1991)). Protein molecular weight standards are commercially available to assist in the estimation of molecular weights of unknown protein (New England Biolabs Inc. Catalog:130–131, 1995; J. L. Hartley, U.S. Pat. No. 5,449,758). However, the molecular weight standards may not correspond closely enough in size to the unknown protein to allow an accurate estimation of apparent molecular weight. The difficulty in estimation of molecular weight is compounded in the case of proteins that are subjected to fragmentation by chemical or enzymatic means, modified by post-translational modification or processing, and/or associated with other proteins in non-covalent complexes.

In addition, the unique nature of the composition of a protein with regard to its specific amino acid constituents results in unique positioning of cleavage sites within the protein. Specific fragmentation of a protein by chemical or enzymatic cleavage results in a unique "peptide fingerprint" (D. W. Cleveland et al., *J. Biol. Chem.* 252:1102–1106, 1977; M. Brown et al., *J. Gen. Virol.* 50:309–316, 1980). Consequently, cleavage at specific sites results in reproducible fragmentation of a given protein into peptides of precise molecular weights. Furthermore, these peptides possess unique charge characteristics that determine the isoelectric pH of the peptide. These unique characteristics can be exploited using a variety of electrophoretic and other techniques (T. D. Brock and M. T. Madigan, *Biology of Microorganisms* 76–77 (Prentice Hall, 6d ed. 1991)).

Fragmentation of proteins is further employed for amino acid composition analysis and protein sequencing (Matsudiara, *J. Biol. Chem.* 262:10035–10038, 1987; C. Eckerskorn et al., *Electrophoresis* 1988, 9:830–838, 1988), particularly the production of fragments from proteins with a "blocked" N-terminus. In addition, fragmented proteins can be used for immunization, for affinity selection (R. A.

Brown, U.S. Pat. No. 5,151,412), for determination of modification sites (eg. phosphorylation), for generation of active biological compounds (T. D. Brock and M. T. Madigan, *Biology of Microorganisms* 300–301 (Prentice Hall, 6d ed. 1991)), and for differentiation of homologous proteins (M. Brown et al., *J. Gen. Virol.* 50:309–316, 1980).

In addition, when a peptide fingerprint of an unknown protein is obtained, it can be compared to a database of known proteins to assist in the identification of the unknown protein using mass spectrometry (W. J. Henzel et al., *Proc. Natl. Acad. Sci. USA* 90:5011–5015, 1993; D. Fenyo et al., *Electrophoresis* 19:998–1005, 1998). A variety of computer software programs to facilitate these comparisons are accessible via the Internet, such as Protein Prospector (Internet site: prospector.uscf.edu), MultiIdent (Internet site: www.expasy.ch/sprot/multiident.html), PeptideSearch (Internet site: www.mann.embl-heiedelberg.de...deSearch/FR_PeptideSearch Form.html), and ProFound (Internet site: www.chait-sgi.rockefeller.edu/cgi-bin/prot-id-frag.html). These programs allow the user to specify the cleavage agent and the molecular weights of the fragmented peptides within a designated tolerance. The programs compare these molecular weights to protein molecular weight information stored in databases to assist in determining the identity of the unknown protein. Accurate information concerning the number of fragmented peptides and the precise molecular weight of those peptides is required for accurate identification. Therefore, increasing the accuracy in determining the number of fragmented peptides and their molecular weight should result in enhanced likelihood of success in the identification of unknown proteins.

In addition, peptide digests of unknown proteins can be sequenced using tandem mass spectrometry (MS/MS) and the resulting sequence searched against databases (J. K. Eng, et al., *J. Am. Soc. Mass Spec.* 5:976–989 (1994); M. Mann and M. Wilm, *Anal. Chem.* 66:4390–4399 (1994); J. A. Taylor and R S. Johnson, *Rapid Comm. Mass Spec.* 11:1067–1075 (1997)). Searching programs that can be used in this process exist on the Internet such as Lutefisk 97 (Internet site: www.Isbc.com:70/Lutefisk97.html), and the Protein Prospector, Peptide Search and ProFound programs described above. Therefore, adding the sequence of a gene and its predicted protein sequence and peptide fragments to a sequence database can aid in the identification of unknown proteins using tandem mass spectrometry.

Thus, there also exists a need in the art for polypeptides suitable for use in peptide fragmentation studies, for use in molecular weight measurements, and for use in protein sequencing using tandem mass spectrometry.

SUMMARY OF THE INVENTION

The invention aids in fulfilling these various needs in the art by providing isolated Death Associated Kinase containing Ankyrin Repeats ("DAKAR") nucleic acids and polypeptides encoded by these nucleic acids. Particular embodiments of the invention are directed to an isolated DAKAR nucleic acid molecule comprising the DNA sequence of SEQ ID NO:1 and an isolated DAKAR nucleic acid molecule encoding the amino acid sequence of SEQ ID NO:2, as well as nucleic acid molecules complementary to these sequences. The invention also encompasses recombinant vectors that direct the expression of the nucleic acid molecules of the invention and host cells stably or transiently transformed or transfected with these vectors.

In addition, the invention encompasses methods of using the nucleic acid noted above to identify nucleic acids encoding proteins having kinase activity or proteins involved in apoptosis signal transduction.

The invention also encompasses isolated polypeptides and fragments thereof encoded by these nucleic acid molecules including soluble polypeptide portions of SEQ ID NO:2. The invention further encompasses methods for the production of these polypeptides, including culturing a host cell under conditions promoting expression and recovering the polypeptide from the culture medium. Especially, the expression of these polypeptides in bacteria, yeast, plant, insect, and animal cells is encompassed by the invention.

In general, the polypeptides of the invention can be used to study cellular processes such as immune regulation, cell death, cell migration, cell-to-cell interaction, and inflammatory responses. In addition, these polypeptides can be used to identify proteins associated with DAKAR kinases.

In addition, the invention includes assays utilizing these polypeptides to screen for potential inhibitors of DAKAR activity. Further, methods of using these polypeptides in the design of inhibitors thereof are also an aspect of the invention.

The invention further provides a method for using these polypeptides as molecular weight markers that allow the estimation of the molecular weight of a protein or a fragmented protein, as well as a method for the visualization of the molecular weight markers of the invention thereof using electrophoresis. The invention further encompasses methods for using the polypeptides of the invention as markers for determining the isoelectric point of an unknown protein, as well as controls for establishing the extent of fragmentation of a protein. Further encompassed by this invention are kits to aid in these determinations.

Further encompassed by this invention is the use of the DAKAR nucleic acid sequences, predicted amino acid sequences of the polypeptide or fragments thereof, or a combination of the predicted amino acid sequences of the polypeptide and fragments thereof for use in searching an electronic database to aid in the identification of sample nucleic acids and/or proteins.

Isolated polyclonal or monoclonal antibodies that bind to these polypeptides are also encompassed by the invention, in addition the use of these antibodies to aid in purifying the DAKAR polypeptide and to inhibit apoptosis.

BRIEF DESCRIPTION OF THE FIGURES

FIG. 1 shows the homology of the DAKAR ankyrin repeats to the known consensus ankyrin repeat sequence.

DETAILED DESCRIPTION OF THE INVENTION

The nucleic acid molecule encompassed in the invention include the following nucleotide sequence:

```
Name: DAKAR
                                        (SEQ ID NO:1)
      1    GGATCCAAAG TGGAGGGCGA GGGCCGGGGC
           CGGTGGGCTC TGGGGCTGCT

51    GCGCACCTTC GACGCCGGCG AATTCGCAGG
           CTGGGAGAAG GTGGGCTCGG

101    GCGGCTTCGG GCAGGTGTAC AAGGTGCGCC
           ATGTGCACTG GAAGACGTGG

151    CTCGCGATCA AGTGCTCGCC CAGTCTGCAC
           GTCGACGACA GGGAACGAAT
```

-continued

```
 201  GGAGCTCCTG GAGGAAGCTA AGAAGATGGA
      GATGGCCAAG TTCCGATACA

251  TTCTACCTGT GTACGGCATA TGCCAGGAAC
      CTGTCGGCTT GGTCATGGAG

301  TACATGGAGA CAGGCTCCCT GGAGAAGCTG
      CTGGCCTCAG AGCCATTGCC

351  TTGGGACCTG CGCTTTCGCA TCGTGCACGA
      GACAGCCGTG GGCATGAACT

401  TCCTGCATTG CATGTCTCCG CCACTGCTGC
      ACCTAGACCT GAAGCCAGCG

451  AACATCCTGC TGGATGCCCA CTACCATGTC
      AAGATTTCTG ACTTTGGGCT

501  GGCCAAGTGC AATGGCATGT CCCACTCTCA
      TGACCTCAGC ATGGATGGCC

551  TGTTTGGTAC AATCGCTTAC CTCCCTCCAG
      AGCGAATTCG TGAAGAGC

601  CGCTTGTTTG ACACCAAACA TGATGTATAC
      AGCTTCGCCA TTGTGATCTG

651  GGGTGTGCTT ACACAGAAGA AGCCATTTGC
      AGATGAAAAG AACATCCTAC

701  ACATCATGAT GAAAGTGGTA AAGGGCCACC
      GCCCAGAGCT GCCACCCATC

751  TGCAGACCCC GGCCGCGTGC CTGTGCCAGC
      CTGATAGGGC TCATGCAACG

801  GTGCTGGCAT GCAGACCCAC AGGTGCGGCC
      CACCTTCCAA GAAATTACCT

851  CTGAAACAGA AGACCTTTGT GAGAAGCCTG
      ATGAGGAGGT GAAAGACCTG

901  GCTCATGAGC CAGGCGAGAA AAGCTCTCTA
      GAGTCCAAGA GTGAGGCCAG

951  GCCCGAGTCC TCACGCCTCA AGCGCGCCTC
      TGCTCCCCCC TTCGATAACG

1001  ACTGCAGTCT CTCCGAGTTG CTGTCACAGT
      TGGACTCTGG GATCTCCCAG

1051  ACTCTTGAAG GCCCCGAAGA GCTCAGCCGA
      AGTTCCTCTG AATGCAAGCT

1101  CCCATCGTCC AGCAGTGGCA AGAGGCTCTC
      GGGGGTGTCC TCAGTGGACT

1151  CAGCCTTTTC CTCCAGAGGA TCGCTGTCAC
      TGTCTTTTGA GCGGGAAGCT

1201  TCAACAGGCG ACCTGGGCCC CACAGACATC
      CAGAAGAAGA AGCTAGTGGA

1251  TGCCATCATA TCAGGGGACA CCAGCAGGCT
      GATGAAGATC CTACAGCCCC

1301  AAGATGTGGA CTTGGTTCTA GACAGCAGTG
      CCAGCCTGCT GCACCTGGCT

1351  GTGGAGGCCG GACAGGAGGA GTGTGTCAAG
      TGGCTGCTGC TTAACAATGC

1401  CAACCCCAAC CTGACCAACA GGAAGGGCTC
      TACACCACTG CATATGGCTG

1451  TGGAGCGGAA GGGACGTGGA ATTGTGGAGC
      TACTGCTAGC CCGGAAGACC

1501  AGTGTCAATG CCAAGGATGA AGACCAGTGG
      ACTGCCCTGC ACTTTGCAGC
```

```
1551  CCAGAATGGG GATGAGGCCA GCACAAGGCT
      GCTGCTAGAA AAGAATGCTT

1601  CTGTCAATGA GGTGGACTTT GAGGGCCGAA
      CACCCATGCA TGTAGCCTGC

1651  CAGCATGGAC AGGAGAACAT TGTGCGCACC
      CTGCTCCGCC GTGGTGTGGA

1701  TGTGGGCCTG CAGGGAAAGG ATGCCTGGTT
      GCCTCTGCAC TATGCTGCCT

1751  GGCAGGGCCA CCTTCCCATT GTTAAGCTGC
      TAGCCAAGCA GCCTGGGGTG

1801  AGTGTGAATG CCCAGACACT AGACGGGAGG
      ACACCCCTGC ACCTGGCTGC

1851  TCAGAGGGGG CATTACCGTG TGGCTCGCAT
      TCTCATTGAC CTGTGCTCTG

1901  ATGTTAACAT CTGCAGCCTA CAGGCACAGA
      CACCTCTGCA TGTTGCTGCA

1951  GAGACTGGAC ACACTAGTAC TGCCAGGCTA
      CTCTTGCATC GTGGTGCTGG

2001  CAAGGAGGCT TTGACCTCAG AGGGCTATAC
      TGCCTTGCAC CTGGCAGCCC

2051  AGAATGGACA CCTGGCTACT GTCAAGCTGC
      TCATAGAGGA GAAGGCTGAT

2101  GTGATGGCTC GGGGTCCCCT GAATCAGACA
      GCACTGCACC TGGCTGCTGC

2151  CCGTGGACAC TCAGAGGTGG TAGAAGAGCT
      GGTCAGTGCT GACCTCATTG

2201  ACCTGTCTGA TGAGCAGGGC CTCAGCGCAC
      TGCACCTGGC TGCTCAGGGC

2251  AGGCATTCAC AGACTGTGGA CACTGCTCTC
      AAACATGGAG CACACATCAA

2301  CTTGCAGAGT CTCAAGTTCC AAGGAGGCCA
      GAGCTCTGCT GCCACGTTGC

2351  TCCGACGCAG CAAGACCTAG
```

The amino acid sequence of the polypeptide encoded by the nucleotide sequence of the invention includes:

Name: DAKAR-polypeptide
(SEQ ID NO:2)

```
  1  MEGEGRGRWA LGLLRTFDAG EFAGWEKVGS
     GGFGQVYKVR HVHWKTWLAI

51  KCSPSLHVDD RERMELLEEA KKMEMAKFRY
     ILPVYGICQE PVGLVMEYME

101  TGSLEKLLAS EPLPWDLRFR IVHETAVGMN
     FLHCMSPPLL HLDLKPANIL

151  LDAHYHVKIS DFGLAKCNGM SHSHDLSMDG
     LFGTIAYLPP ERIREKSRLF

201  DTKHDVYSFA IVIWGVLTQK KPFADEKNIL
     HIMMKVVKGH RPELPPICRP

251  RPRACASLIG LMQRCWHADP QVRPTFQEIT
     SETEDLCEKP DEEVKDLAHE

301  PGEKSSLESK SEARPESSRL KRASAPPFDN
     DCSLSELLSQ LDSGISQTLE
```

```
351   GPEELSRSSS ECKLPSSSSG KRLSGVSSVD
      SAFSSRGSLS LSFEREASTG

401   DLGPTDIQKK KLVDAIISGD TSRLMKILQP
      QDVDLVLDSS ASLLHLAVEA

451   GQEECVKWLL LNNANPNLTN RKGSTPLHMA
      VERKGRGIVE LLLARKTSVN

501   AKDEDQWTAL HFAAQNGDEA STRLLLEKNA
      SVNEVDFEGR TPMHVACQHG

551   QENIVRTLLR RGVDVGLQGK DAWLPLHYAA
      WQGHLPIVKL LAKQPGVSVN

601   AQTLDGRTPL HLAAQRGHYR VARILIDLCS
      DVNICSLQAQ TPLHVAAETG

651   HTSTARLLLH RGAGKEALTS EGYTALHLAA
      QNGHLATVKL LIEEKADVMA

701   RGPLNQTALH LAAARGHSEV VEELVSADLI
      DLSDEQGLSA LHLAAQGRHS

751   QTVETLLKHG AHINLQSLKF QGGQSSAATL LRRSKT
```

The discovery of the nucleic acid of the invention enables the construction of expression vectors comprising nucleic acid sequences encoding polypeptides; host cells transfected or transformed with the expression vectors; isolated and purified biologically active polypeptides and fragments thereof. The invention also enables the use of the nucleic acids or oligonucleotides thereof as probes to identify nucleic acid encoding proteins having kinase activity. The discovery further permits the use of such polypeptides and soluble fragments to function as a kinase. The polypeptides and fragments can also generate antibodies which can be used for the purification of the polypeptides of the invention. Finally, the invention enables the use of such polypeptides and fragmented peptides as molecular weight markers; the use of such polypeptides and fragmented peptides as controls for peptide fragmentation, and kits comprising these reagents.

Nucleic Acid Molecules

In a particular embodiment, the invention relates to certain isolated nucleotide sequences that are free from contaminating endogenous material. A "nucleotide sequence" refers to a polynucleotide molecule in the form of a separate fragment or as a component of a larger nucleic acid construct The nucleic acid molecule has been derived from DNA or RNA isolated at least once in substantially pure form and in a quantity or concentration enabling identification, manipulation, and recovery of its component nucleotide sequences by standard biochemical methods (such as those outlined in Sambrook et al., *Molecular Cloning: A Laboratory Manual,* 2nd sed., Cold Spring Harbor Laboratory, Cold Spring Harbor, N.Y. (1989)). Such sequences are preferably provided and/or constructed in the form of an open reading frame uninterrupted by internal non-translated sequences, or introns, that are typically present in eukaryotic genes. Sequences of non-translated DNA can be present 5' or 3' from an open reading frame, where the same do not interfere with manipulation or expression of the coding region.

Nucleic acid molecules of the invention include DNA in both single-stranded and double-stranded form, as well as the RNA complement thereof. DNA includes, for example, cDNA, genomic DNA, chemically synthesized DNA, DNA amplified by PCR, and combinations thereof. Genomic DNA may be isolated by conventional techniques, e.g., using the cDNA of SEQ ID NO:1, or a suitable fragment thereof, as a probe.

The DNA molecules of the invention include full length genes as well as polynucleotides and fragments thereof. Other embodiments include DNA encoding a truncated version of the kinase containing, for example, only the kinase catalytic domain or a catalytically inactive mutant thereof. The nucleic acids of the invention are preferentially derived from murine sources, but the invention includes those derived from other species, as well.

Preferred Sequences

A particularly preferred nucleotide sequence of the invention is SEQ ID NO:1, as set forth above. A cDNA clone having the nucleotide sequence of SEQ ID NO:1 was isolated as described in Example 1. The sequences of amino acids encoded by the DNA of SEQ ID NO:1 is shown in SEQ ID NO:2. This sequence identifies the DAKAR polynucleotide as a member of a family of protein kinases involved in apoptosis. These proteins are characterized by an N-terminal protein serine-threonine kinase domain and a C-terminal domain which is variable and may include a series of ankyrin repeats, a death domain, or a caspase-recruitment domain. In the case of DAKAR, the C-terminal contains a series of ankyrin repeats, such as those known in other proteins to mediate protein-protein interactions. The kinase domain of DAKAR shares homology with three known proteins (RICK, DAPK-1, and RIP) that have been shown to play a role in apoptosis.

Additional Sequences

Due to the known degeneracy of the genetic code, wherein more than one codon can encode the same amino acid, a DNA sequence can vary from that shown in SEQ ID NO:1, and still encode a polypeptide having the amino acid sequence of SEQ ID NO:2. Such variant DNA sequences can result from silent mutations (e.g., occurring during PCR amplification), or can be the product of deliberate mutagenesis of a native sequence.

The invention thus provides isolated DNA sequences encoding polypeptides of the invention, selected from: (a) DNA comprising the nucleotide sequence of SEQ ID NO:1; (b) DNA encoding the polypeptides of SEQ ID NO:2; (c) DNA capable of hybridization to a DNA of (a) or (b) under conditions of moderate stringency and which encodes polypeptides of the invention; (d) DNA capable of hybridization to a DNA of (a) or (b) under conditions of high stringency and which encodes polypeptides of the invention, and (e) DNA which is degenerate as a result of the genetic code to a DNA defined in (a), (b), (c), or (d) and which encode polypeptides of the invention. Of course, polypeptides encoded by such DNA sequences are encompassed by the invention.

As used herein, conditions of moderate stringency can be readily determined by those having ordinary skill in the art based on, for example, the length of the DNA. The basic conditions are set forth by Sambrook et al. *Molecular Cloning: A Laboratory Manual,* 2 ed. Vol. 1, pp. 1.101–104, Cold Spring Harbor Laboratory Press, (1989), and include use of a prewashing solution for the nitrocellulose filters 5×SSC, 0.5% SDS, 1.0 mM EDTA (pH 8.0), hybridization conditions of about 50% formamide, 6×SSC at about 42° C. (or other similar hybridization solution, such as Stark's solution, in about 50% formamide at about 42° C.), and washing conditions of about 60° C., 0.5×SSC, 0.1% SDS. Conditions of high stringency can also be readily determined by the skilled artisan based on, for example, the length of the DNA. Generally, such conditions are defined as hybridization conditions as above, and with washing at approximately 68° C., 0.2×SSC, 0.1% SDS. The skilled artisan will recognize that the temperature and wash solution salt concentration can be adjusted as necessary according to factors such as the length of the probe.

In another embodiment, the nucleic acid molecules of the invention also comprise nucleotide sequences that are at least 80% identical to a native sequence. Also contemplated are embodiments in which a nucleic acid molecule comprises a sequence that is at least 90% identical, at least 95% identical, at least 98% identical, at least 99% identical, or at least 99.9% identical to a native sequence.

The percent identity may be determined by visual inspection and mathematical calculation. Alternatively, the percent identity of two nucleic acid sequences can be determined by comparing sequence information using the GAP computer program, version 6.0 described by Devereux et al. (*Nucl. Acids Res.* 12:387, 1984) and available from the University of Wisconsin Genetics Computer Group (UWGCG). The preferred default parameters for the GAP program include: (1) a unary comparison matrix (containing a value of 1 for identities and 0 for non-identities) for nucleotides, and the weighted comparison matrix of Gribskov and Burgess, *Nucl. Acids Res.* 14:6745, 1986, as described by Schwartz and Dayhoff, eds., *Atlas of Protein Sequence and Structure*, National Biomedical Research Foundation, pp. 353–358, 1979; (2) a penalty of 3.0 for each gap and an additional 0.10 penalty for each symbol in each gap; and (3) no penalty for end gaps. Other programs used by one skilled in the art of sequence comparison may also be used.

The invention also provides isolated nucleic acids useful in the production of polypeptides. Such polypeptides may be prepared by any of a number of conventional techniques. A DNA sequence encoding a DAKAR polypeptide, or desired fragment thereof may be subcloned into an expression vector for production of the polypeptide or fragment. The DNA sequence advantageously is fused to a sequence encoding a suitable leader or signal peptide. Alternatively, the desired fragment may be chemically synthesized using known techniques. DNA fragments also may be produced by restriction endonuclease digestion of a full length cloned DNA sequence, and isolated by electrophoresis on agarose gels. If necessary, oligonucleotides that reconstruct the 5' or 3' terminus to a desired point may be ligated to a DNA fragment generated by restriction enzyme digestion. Such oligonucleotides may additionally contain a restriction endonuclease cleavage site upstream of the desired coding sequence, and position an initiation codon (ATG) at the N-terminus of the coding sequence.

The well-known polymerase chain reaction (PCR) procedure also may be employed to isolate and amplify a DNA sequence encoding a desired protein fragment. Oligonucleotides that define the desired termini of the DNA fragment are employed as 5' and 3' primers. The oligonucleotides may additionally contain recognition sites for restriction endonucleases, to facilitate insertion of the amplified DNA fragment into an expression vector. PCR techniques are described in Saiki et al., *Science* 239:487 (1988); *Recombinant DNA Methodology*, Wu et al., eds., Academic Press, Inc., San Diego (1989), pp. 189–196; and *PCR Protocols: A Guide to Methods and Applications*, Innis et al., eds., Academic Press, Inc. (1990).

Polypeptides and Fragments Thereof

The invention encompasses polypeptides and fragments thereof in various forms, including those that are naturally occurring or produced through various techniques such as procedures involving recombinant DNA technology. Such forms include, but are not limited to, derivatives, variants, and oligomers, as well as fusion proteins or fragments thereof.

Polypeptides and Fragments Thereof

The polypeptides of the invention include full length proteins (amino acids 1 to 786 of SEQ ID NO:2) encoded by the nucleic acid sequences set forth above. Particularly preferred polypeptides comprise the amino acid sequence of SEQ ID NO:2 with particularly preferred fragments comprising amino acids 1 to 280 and 281 to 786 of SEQ ID NO:2. Additional preferred regions are the N-terminal kinase domain (amino acids 17 to 297) and a C-terminal series of nine tandem ankyrin repeats (amino acids 471 to 768) of SEQ ID NO:2.

The invention also provides polypeptides and fragments of the kinase domain and polypeptides and fragments of the ankyrin repeats, individually or any combination thereof, that retain a desired biological activity. Particular embodiments are directed to polypeptide fragments that retain the ability to bind "binding partners", native cognates, substrates, or counter-structures. In another embodiment, the polypeptides and fragments advantageously include regions that are conserved in the DAKAR family as described above.

Also provided herein are polypeptide fragments comprising at least 20, or at least 30, contiguous amino acids of the sequence of SEQ ID NO:2. Fragments derived from different domains find use in studies of signal transduction, and in regulating cellular processes associated with transduction of biological signals. Polypeptide fragments also may be employed as immunogens, in generating antibodies.

Variants

Naturally occurring variants as well as derived variants of the polypeptides and fragments are provided herein.

Variants may exhibit amino acid sequences that are at least 80% identical. Also contemplated are embodiments in which a polypeptide or fragment comprises an amino acid sequence that is at least 90% identical, at least 95% identical, at least 98% identical, at least 99% identical, or at least 99.9% identical to the preferred polypeptide or fragment thereof Percent identity may be determined by visual inspection and mathematical calculation. Alternatively, the percent identity of two protein sequences can be determined by comparing sequence information using the GAP computer program, based on the algorithm of Needleman and Wunsch (J. Mol. Bio. 48:443, 1970) and available from the University of Wisconsin Genetics Computer Group (UWGCG). The preferred default parameters for the GAP program include: (1) a scoring matrix, blosum62, as described by Henikoff and Henikoff (Proc. Natl. Acad. Sci. USA 89:10915, 1992); (2) a gap weight of 12; (3) a gap length weight of 4; and (4) no penalty for end gaps. Other programs used by one skilled in the art of sequence comparison may also be used.

The variants of the invention include, for example, those that result from alternate mRNA splicing events or from proteolytic cleavage. Alternate splicing of mRNA may, for example, yield a truncated but biologically active protein. Variations attributable to proteolysis include, for example, differences in the N- or C-termini upon expression in different types of host cells, due to proteolytic removal of one or more terminal amino acids from the protein (generally from 1–5 terminal amino acids). Proteins in which differences in amino acid sequence are attributable to genetic polymorphism (allelic variation among individuals producing the protein) are also contemplated herein.

Additional variants within the scope of the invention include polypeptides that may be modified to create derivatives thereof by forming covalent or aggregative conjugates with other chemical moieties, such as glycosyl groups, lipids, phosphate, acetyl groups and the like. Covalent derivatives may be prepared by linking the chemical moieties to functional groups on amino acid side chains or at the N-terminus or C-terminus of a polypeptide. Conjugates comprising diagnostic (detectable) attached thereto are within the scope of the invention herein.

Other derivatives include covalent or aggregative conjugates of the polypeptides with other proteins or polypeptides, such as by synthesis in recombinant culture as N-terminal or C-terminal fusions. Examples of fusion proteins are discussed below in connection with oligomers. Further, fusion proteins can comprise peptides added to facilitate purification and identification. Such peptides include, for example, poly-His or the antigenic identification peptides described in U.S. Pat. No. 5,011,912 and in Hopp et al., *Bio/Technology* 6:1204, 1988. One such peptide is the FLAG® peptide, Asp-Tyr-Lys-Asp-Asp-Asp-Asp-Lys (SEQ ID NO:3), which is highly antigenic and provides an epitope reversibly bound by a specific monoclonal antibody, enabling rapid assay and facile purification of expressed recombinant protein. A murine hybridoma designated 4E11 produces a monoclonal antibody that binds the FLAG® peptide in the presence of certain divalent metal cations, as described in U.S. Pat. No. 5,011,912, hereby incorporated by reference. The 4E11 hybridoma cell line has been deposited with the American Type Culture Collection.

Among the variant polypeptides provided herein are variants of native polypeptides that retain the native biological activity or the substantial equivalent thereof. One example is a variant that binds with essentially the same binding affinity as does the native form. Binding affinity can be measured by conventional procedures, e.g., as described in U.S. Pat. No. 5,512,457 and as set forth below.

Variants include polypeptides that are substantially homologous to the native form, but which have an amino acid sequence different from that of the native form because of one or more deletions, insertions or substitutions. For example, catalytically inactivated variants in which, for example, the invariant lysine residue (amino acid 51 in SEQ ID NO:2) of kinase subdomain II is substituted for an arginine or alanine, or in which the invariant glycine residue (s) (amino acids 29, 31 and/or 34 of SEQ ID NO:2) are substituted for any other amino acid. Other particular embodiments include, but are not limited to, polypeptides that comprise from one to ten deletions, insertions or substitutions of amino acid residues, when compared to a native sequence.

A given amino acid may be replaced, for example, by a residue having similar physiochemical characteristics. Examples of such conservative substitutions include substitution of one aliphatic residue for another, such as Ile, Val, Leu, or Ala for one another; substitutions of one polar residue for another, such as between Lys and Arg, Glu and Asp, or Gln and Asn; or substitutions of one aromatic residue for another, such as Phe, Trp, or Tyr for one another. Other conservative substitutions, e.g., involving substitutions of entire regions having similar hydrophobicity characteristics, are well known.

Similarly, the DNAs of the invention include variants that differ from a native DNA sequence because of one or more deletions, insertions or substitutions, but that encode a biologically active polypeptide.

In another example of variants, sequences encoding Cys residues that are not essential for biological activity can be altered to cause the Cys residues to be deleted or replaced with other amino acids, preventing formation of incorrect intramolecular disulfide bridges upon folding or renaturation.

Other variants are prepared by modification of adjacent dibasic amino acid residues, to enhance expression in yeast systems in which KEX2 protease activity is present. EP 212,914 discloses the use of site-specific mutagenesis to inactivate KEX2 protease processing sites in a protein. KEX2 protease processing sites are inactivated by deleting, adding or substituting residues to alter Arg-Arg, Arg-Lys, and Lys-Arg pairs to eliminate the occurrence of these adjacent basic residues. Lys-Lys pairings are considerably less susceptible to KEX2 cleavage, and conversion of Arg-Lys or Lys-Arg to Lys-Lys represents a conservative and preferred approach to inactivating KEX2 sites.

Oligomers

Encompassed by the invention are oligomers or fusion proteins that contain DAKAR polypeptides. When the polypeptide is a soluble peptide such as the polypeptides of the invention, fusion partners are linked to either the N- or C-terminus. Such oligomers may be in the form of covalently-linked or non-covalently-linked multimers, including dimers, trimers, or higher oligomers. In one aspect of the invention, the oligomers maintain the binding ability of the polypeptide components and provide therefor, bivalent, trivalent, etc., binding sites.

One embodiment of the invention is directed to oligomers comprising multiple polypeptides joined via covalent or non-covalent interactions between peptide moieties fused to the polypeptides. Such peptides may be peptide linkers (spacers), or peptides that have the property of promoting oligomerization. Leucine zippers and certain polypeptides derived from antibodies are among the peptides that can promote oligomerization of the polypeptides attached thereto, as described in more detail below.

Immunoglobulin-based Oligomers

As one alternative, an oligomer is prepared using polypeptides derived from immunoglobulins. Preparation of fusion proteins comprising certain heterologous polypeptides fused to various portions of antibody-derived polypeptides (including the Fc domain) has been described, e.g., by Ashkenazi et al. (*PNAS USA* 88:10535, 1991); Byrn et al. (*Nature* 344:677, 1990); and Hollenbaugh and Aruffo ("Construction of Immunoglobulin Fusion Proteins", in *Current Protocols in Immunology*, Suppl. 4, pages 10.19.1–10.19.11, 1992).

One embodiment of the present invention is directed to a dimer comprising two fusion proteins created by fusing a polypeptide of the invention to an Fc polypeptide derived from an antibody. A gene fusion encoding the polypeptide/Fc fusion protein is inserted into an appropriate expression vector. Polypeptide/Fc fusion proteins are expressed in host cells transformed with the recombinant expression vector, and allowed to assemble much like antibody molecules, whereupon interchain disulfide bonds form between the Fc moieties to yield divalent molecules.

The term "Fc polypeptide" as used herein includes native and mutein forms of polypeptides made up of the Fc region of an antibody comprising any or all of the CH domains of the Fc region. Truncated forms of such polypeptides containing the hinge region that promotes dimerization are also included. Preferred polypeptides comprise an Fc polypeptide derived from a human IgG1 antibody.

One suitable Fc polypeptide, described in PCT application WO 93/10151 (hereby incorporated by reference), is a single chain polypeptide extending from the N-terminal hinge region to the native C-terminus of the Fc region of a human IgG1 antibody. Another useful Fc polypeptide is the Fc mutein described in U.S. Pat. No. 5,457,035 and in Baum et al., (*EMBO J.* 13:3992–4001, 1994) incorporated herein by reference. The amino acid sequence of this mutein is identical to that of the native Fc sequence presented in WO 93/10151, except that amino acid 19 has been changed from Leu to Ala, amino acid 20 has been changed from Leu to Glu, and amino acid 22 has been changed from Gly to Ala. The mutein exhibits reduced affinity for Fc receptors.

The above-described fusion proteins comprising Fc moieties (and oligomers formed therefrom) offer the advantage of facile purification by affinity chromatography over Protein A or Protein G columns.

In other embodiments, the polypeptides of the invention may be substituted for the variable portion of an antibody heavy or light chain. If fusion proteins are made with both heavy and light chains of an antibody, it is possible to form an oligomer with as many as four DAKAR polypeptides.

Peptide-linker Based Oligomers

Alternatively, the oligomer is a fusion protein comprising multiple polypeptides, with or without peptide linkers (spacer peptides). Among the suitable peptide linkers are those described in U.S. Pat. Nos. 4,751,180 and 4,935,233, which are hereby incorporated by reference. A DNA sequence encoding a desired peptide linker may be inserted between, and in the same reading frame as, the DNA sequences of the invention, using any suitable conventional technique. For example, a chemically synthesized oligonucleotide encoding the linker may be ligated between the sequences. In particular embodiments, a fusion protein comprises from two to four soluble DAKAR polypeptides, separated by peptide linkers.

Leucine-Zippers

Another method for preparing the oligomers of the invention involves use of a leucine zipper. Leucine zipper domains are peptides that promote oligomerization of the proteins in which they are found. Leucine zippers were originally identified in several DNA-binding proteins (Landschulz et al., *Science* 240:1759, 1988), and have since been found in a variety of different proteins. Among the known leucine zippers are naturally occurring peptides and derivatives thereof that dimerize or trimerize.

The zipper domain (also referred to herein as an oligomerizing, or oligomer-forming, domain) comprises a repetitive heptad repeat, of ten with four or five leucine residues interspersed with other amino acids. Examples of zipper domains are those found in the yeast transcription factor GCN4 and a heat-stable DNA-binding protein found in rat liver (C/EBP; Landschulz et al., *Science* 243:1681, 1989). Two nuclear transforming proteins, fos and jun, also exhibit zipper domains, as does the gene product of the murine proto-oncogene, c-myc (Landschulz et al., *Science* 240:1759, 1988). The products of the nuclear oncogenes fos and jun comprise zipper domains that preferentially form heterodimer (O'Shea et al., *Science* 245:646, 1989, Turner and Tjian, *Science* 243:1689, 1989). The zipper domain is necessary for biological activity (DNA binding) in these proteins.

The fusogenic proteins of several different viruses, including paramyxovirus, coronavirus, measles virus and many retroviruses, also possess zipper domains (Buckland and Wild, *Nature* 338:547,1989; Britton, *Nature* 353:394, 1991; Delwart and Mosialos, *AIDS Research and Human Retroviruses* 6:703, 1990). The zipper domains in these fusogenic viral proteins are near the transmembrane region of the proteins; it has been suggested that the zipper domains could contribute to the oligomeric structure of the fusogenic proteins. Oligomerization of fusogenic viral proteins is involved in fusion pore formation (Spruce et al, *Proc. Natl. Acad. Sci. U.S.A.* 88:3523, 1991). Zipper domains have also been recently reported to play a role in oligomerization of heat-shock transcription factors (Rabindran et al., *Science* 259:230, 1993).

Zipper domains fold as short, parallel coiled coils (O'Shea et al., *Science* 254:539; 1991). The general architecture of the parallel coiled coil has been well characterized, with a "knobs-into-holes" packing as proposed by Crick in 1953 (*Acta Crystallogr.* 6:689). The dimer formed by a zipper domain is stabilized by the heptad repeat, designated $(abcdefg)_n$ according to the notation of McLachlan and Stewart (*J. Mol. Biol.* 98:293; 1975), in which residues a and d are generally hydrophobic residues, with d being a leucine, which line up on the same face of a helix. Oppositely-charged residues commonly occur at positions g and e. Thus, in a parallel coiled coil formed from two helical zipper domains, the "knobs" formed by the hydrophobic side chains of the first helix are packed into the "holes" formed between the side chains of the second helix.

The residues at position d (often leucine) contribute large hydrophobic stabilization energies, and are important for oligomer formation (Krystek: et al., *Int. J. Peptide Res.* 38:229, 1991). Lovejoy et al. (*Science* 259:1288, 1993) recently reported the synthesis of a triple-stranded α-helical bundle in which the helices run up-up-down. Their studies confirmed that hydrophobic stabilization energy provides the main driving force for the formation of coiled coils from helical monomers. These studies also indicate that electrostatic interactions contribute to the stoichiometry and geometry of coiled coils. Further discussion of the structure of leucine zippers is found in Harbury et al (*Science* 262:1401, Nov. 26, 1993).

Examples of leucine zipper domains suitable for producing soluble oligomeric proteins are described in PCT application WO 94/10308, as well as the leucine zipper derived from lung surfactant protein D (SPD) described in Hoppe et al. (*FEBS Letters* 344:191, 1994), hereby incorporated by reference. The use of a modified leucine zipper that allows for stable trimerization of a heterologous protein fused thereto is described in Fanslow et al. (*Semin. Immunol.* 6:267–278, 1994). Recombinant fusion proteins comprising a soluble polypeptide fused to a leucine zipper peptide are expressed in suitable host cells, and the soluble oligomer that forms is recovered from the culture supernatant.

Certain leucine zipper moieties preferentially form trimers. One example is a leucine zipper derived from lung surfactant protein D (SPD) noted above, as described in Hoppe et al. (*FEBS Letters* 344:191, 1994) and in U.S. Pat. No. 5,716,805, hereby incorporated by reference in their entirety. This lung SPD-derived leucine zipper peptide comprises the amino acid sequence Pro Asp Val Ala Ser Leu Arg Gln Gln Val Glu Ala Leu Gin Gly Gln Val Gln His Leu Gin Ala Ala Phe Ser Gin Tyr (SEQ ID NO:4).

Another example of a leucine zipper that promotes trimerization is a peptide comprising the amino acid sequence Arg Met Lys Gin Ile Glu Asp Lys Ile Glu Glu Ile Leu Ser Lys Ile Tyr His Ile Glu Asn Glu Ile Ala Arg Ile Lys Lys Leu Ile Gly Glu Arg (SEQ ID NO:5), as described in U.S. Pat. No. 5,716,805. In one alternative embodiment, an N-terminal Asp residue is added; in another, the peptide lacks the N-terminal Arg residue.

Fragments of the foregoing zipper peptides that retain the property of promoting oligomerization may be employed as well. Examples of such fragments include, but are not limited to, peptides lacking one or two of the N-terminal or C-terminal residues presented in the foregoing amino acid sequences. Leucine zippers may be derived from naturally occurring leucine zipper peptides, e.g., via conservative substitution(s) in the native amino acid sequence, wherein the peptide's ability to promote oligomerization is retained.

Other peptides derived from naturally occurring trimeric proteins may be employed in preparing trimeric DAKAR. Alternatively, synthetic peptides that promote oligomerization may be employed. In particular embodiments, leucine residues in a leucine zipper moiety are replaced by isoleucine residues. Such peptides comprising isoleucine may be referred to as isoleucine zippers, but are encompassed by the term "leucine zippers" as employed herein.

Production of Polypeptides and Fragments Thereof

Expression, isolation and purification of the polypeptides and fragments of the invention may be accomplished by any suitable technique., including but not limited to the following:

Expression Systems

The present invention also provides recombinant cloning and expression vectors containing DNA, as well as host cell containing the recombinant vectors. Expression vectors comprising DNA may be used to prepare the polypeptides or fragments of the invention encoded by the DNA. A method for producing polypeptides comprises culturing host cells transformed with a recombinant expression vector encoding the polypeptide, under conditions that promote expression of the polypeptide, then recovering the expressed polypeptides from the culture. The skilled artisan will recognize that the procedure for purifying the expressed polypeptides will vary according to such factors as the type of host cells employed, and whether the polypeptide is membrane-bound or a soluble form that is secreted from the host cell.

Any suitable expression system may be employed. The vectors include a DNA encoding a polypeptide or fragment of the invention, operably linked to suitable transcriptional or translational regulatory nucleotide sequences, such as those derived from a mammalian, microbial, viral, or insect gene. Examples of regulatory sequences include transcriptional promoters, operators, or enhancers, an mRNA ribosomal binding site, and appropriate sequences which control transcription and translation initiation and termination. Nucleotide sequences are operably linked when the regulatory sequence functionally relates to the DNA sequence. Thus, a promoter nucleotide sequence is operably linked to a DNA sequence if the promoter nucleotide sequence controls the transcription of the DNA sequence. An origin of replication that confers the ability to replicate in the desired host cells, and a selection gene by which transformants are identified, are generally incorporated into the expression vector.

In addition, a sequence encoding an appropriate signal peptide can be incorporated into expression vectors. A DNA sequence for a signal peptide (secretory leader) may be fused in frame to the nucleic acid sequence of the invention so that the DNA is initially transcribed, and the mRNA translated, into a fusion protein comprising the signal peptide. A signal peptide that is functional in the intended host cells promotes extracellular secretion of the polypeptide. The signal peptide is cleaved from the polypeptide upon secretion of polypeptide from the cell.

The skilled artisan will also recognize that the position(s) at which the signal peptide is cleaved may differ from that predicted by computer program, and may vary according to such factors as the type of host cells employed in expressing a recombinant polypeptide. A protein preparation may include a mixture of protein molecules having different N-terminal amino acids, resulting from cleavage of the signal peptide at more than one site.

Suitable host cells for expression of polypeptides include prokaryotes, yeast or higher eukaryotic cells. Mammalian or insect cells are generally preferred for use as host cells. Appropriate cloning and expression vectors for use with bacterial, fungal, yeast, and mammalian cellular hosts are described, for example, in Pouwels et al. *Cloning Vectors: A Laboratory Manual,* Elsevier, New York, (1985). Cell-free translation systems could also be employed to produce polypeptides using RNAs derived from DNA constructs disclosed herein.

Prokaryotic Systems

Prokaryotes include gram-negative or gram-positive organisms. Suitable prokaryotic host cells for transformation include, for example, *E. coli, Bacillus subtilis, Salmonella typhimurium,* and various other species within the genera Pseudomonas, Streptomyces, and Staphylococcus. In a prokaryotic host cell, such as *E. coli,* a polypeptide may include an N-terminal methionine residue to facilitate expression of the recombinant polypeptide in the prokaryotic host cell. The N-terminal Met may be cleaved from the expressed recombinant polypeptide.

Expression vectors for use in prokaryotic host cells generally comprise one or more phenotypic selectable marker genes. A phenotypic selectable marker gene is, for example, a gene encoding a protein that confers antibiotic resistance or that supplies an autotrophic requirement. Examples of useful expression vectors for prokaryotic host cells include those derived from commercially available plasmids such as the cloning vector pBR322 (ATCC 37017). pBR322 contains genes for ampicillin and tetracycline resistance and thus provides simple means for identifying transformed cells. An appropriate promoter and a DNA sequence are inserted into the pBR322 vector. Other commercially available vectors include, for example, pKK223-3 (Pharmacia Fine Chemicals, Uppsala, Sweden) and pGEM1 (Promega Biotec, Madison, Wis., USA).

Promoter sequences commonly used for recombinant prokaryotic host cell expression vectors include β-lactamase (penicillinase), lactose promoter system (Chang et al., *Nature* 275:615, 1978; and Goeddel et al., *Nature* 281:544, 1979), tryptophan (trp) promoter system (Goeddel et al., *Nucl. Acids Res.* 8:4057, 1980; and EP-A-36776) and tac promoter (Maniatis, *Molecular Cloning: A Laboratory Manual,* Cold Spring Harbor Laboratory, p. 412, 1982). A particularly useful prokaryotic host cell expression system employs a phage $\lambda P_L$ promoter and a cI857ts thermolabile repressor sequence. Plasmid vectors available from the American Type Culture Collection which incorporate derivatives of the $\lambda P_L$ promoter include plasmid pHUB2 (resident in *E. coli* strain JMB9, ATCC 37092) and pPLc28 (resident in *E. coli* RR1, ATCC 53082).

Yeast Systems

Alternatively, the polypeptides may be expressed in yeast host cells, preferably from the Saccharomyces genus (e.g., *S. cerevisiae*). Other genera of yeast, such as Pichia or Kluyveromyces, may also be employed. Yeast vectors will often contain an origin of replication sequence from a 2μ yeast plasmid, an autonomously replicating sequence (AR S), a promoter region, sequences for polyadenylation, sequences for transcription termination, and a selectable marker gene. Suitable promoter sequences for yeast vectors include, among others, promoters for metallothionein, 3-phosphoglycerate kinase (Hitzeman et al., *J. Biol. Chem.* 255:2073, 1980) or other glycolytic enzymes (Hess et al., *J. Adv. Enzyme Reg.* 7:149, 1968; and Holland et al., *Biochem.* 17:4900, 1978), such as enolase, glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phospho-glucose isomerase, and glucokinase. Other suitable vectors and promoters for use in yeast expression are further described in Hitzeman, EPA-73,657. Another alternative is the glucose-repressible ADH2 promoter described by Russell et al. (*J. Biol. Chem.* 258:2674, 1982) and Beier et al. (*Nature* 300:724, 1982). Shuttle vectors replicable in both yeast and *E. coli* may be constructed by inserting DNA sequences from pBR322 for selection and replication in *E. coli* (Amp$^r$ gene and origin of replication) into the above-described yeast vectors.

The yeast α-factor leader sequence may be employed to direct secretion of the polypeptide. The α-factor leader sequence is often inserted between the promoter sequence and the structural gene sequence. See, e.g., Kurjan et al., *Cell* 30:933, 1982 and Bitter et al., *Proc. Natl. Acad. Sci. USA* 81:5330, 1984. Other leader sequences suitable for facilitating secretion of recombinant polypeptides from yeast hosts are known to those of skill in the art. A leader sequence may be modified near its 3' end to contain one or more restriction sites. This will facilitate fusion of the leader sequence to the structural gene.

Yeast transformation protocols are known to those of skill in the art. One such protocol is described by Hinnen et al., *Proc. Natl. Acad. Sci. USA* 75:1929, 1978. The Hinnen et al. protocol selects for Trp$^+$ transformants in a selective medium, wherein the selective medium consists of 0.67% yeast nitrogen base, 0.5% casamino acids, 2% glucose, 10 mg/ml adenine and 20 mg/ml uracil.

Yeast host cells transformed by vectors containing an ADH2 promoter sequence may be grown for inducing expression in a "rich" medium. An example of a rich medium is one consisting of 1% yeast extract, 2% peptone, and 1% glucose supplemented with 80 mg/ml adenine and 80 mg/ml uracil. Derepression of the ADH2 promoter occurs when glucose is exhausted from the medium.

Mammalian or Insect Systems

Mammalian or insect host cell culture systems also may be employed to express recombinant polypeptides. Bacculovirus systems for production of heterologous proteins in insect cells are reviewed by Luckow and Summers, *Bio/Technology* 6:47 (1988). Established cell lines of mammalian origin also may be employed. Examples of suitable mammalian host cell lines include the COS-7 line of monkey kidney cells (ATCC CRL 1651) (Gluzman et al., *Cell* 23:175, 1981), L cells, C127 cells, 3T3 cells (ATCC CCL 163), Chinese hamster ovary (CHO) cells, HeLa cells, and BHK (ATCC CRL 10) cell lines, and the CV1/EBNA cell line derived from the African green monkey kidney cell line CV1 (ATCC CCL 70) as described by McMahan et al. (*EMBO J.* 10: 2821, 199 1).

Established methods for introducing DNA into mammalian cells have been described (Kaufman, R. J., *Large Scale Mammalian Cell Culture*, 1990, pp. 15–69). Additional protocols using commercially available reagents, such as Lipofectamine lipid reagent (Gibco/BRL) or Lipofectamine-Plus lipid reagent, can be used to transfect cells (Felgner et al., *Proc. Natl. Acad. Sci. USA* 84:7413–7417, 1987). In addition, electroporation can be used to transfect mammalian cells using conventional procedures, such as those in Sambrook et al. (*Molecular Cloning. A Laboratory Manual*, 2 ed. Vol. 1–3, Cold Spring Harbor Laboratory Press, 1989). Selection of stable transformants can be performed using methods known in the art, such as, for example, resistance to cytotoxic drugs. Kaufman et al., *Meth. in Enzymology* 185:487–511, 1990, describes several selection schemes, such as dihydrofolate reductase (DHFR) resistance. A suitable host strain for DHFR selection can be CHO strain DX-B11, which is deficient in DHFR (Urlaub and Chasin, *Proc. Natl. Acad. Sci. USA* 77:4216–4220, 1980). A plasmid expressing the DHFR cDNA can be introduced into strain DX-B11, and only cells that contain the plasmid can grow in the appropriate selective media. Other examples of selectable markers that can be incorporated into an expression vector include cDNAs conferring resistance to antibiotics, such as G418 and hygromycin B. Cells harboring the vector can be selected on the basis of resistance to these compounds.

Transcriptional and translational control sequences for mammalian host cell expression vectors can be excised from viral genomes. Commonly used promoter sequences and enhancer sequences are derived from polyoma virus, adenovirus 2, simian virus 40 (SV40), and human cytomegalovirus. DNA sequences derived from the SV40 viral genome, for example, SV40 origin, early and late promoter, enhancer, splice, and polyadenylation sites can be used to provide other genetic elements for expression of a structural gene sequence in a mammalian host cell. Viral early and late promoters are particularly useful because both are easily obtained from a viral genome as a fragment, which can also contain a viral origin of replication (Fiers et al., *Nature* 273:113, 1978; Kaufman, *Meth. in Enzymology*, 1990). Smaller or larger SV40 fragments can also be used, provided the approximately 250 bp sequence extending from the Hind III site toward the Bgl I site located in the SV40 viral origin of replication site is included.

Additional control sequences shown to improve expression of heterologous genes from mammalian expression vectors include such elements as the expression augmenting sequence element (EASE) derived from CHO cells (Morris et al., *Animal Cell Technology*, 1997, pp. 529–534 and PCT Application WO 97/25420) and the tripartite leader (TPL) and VA gene RNAs from Adenovirus 2 (Gingeras et al., *J. Biol. Chem.* 257:13475–13491, 1982). The internal ribosome entry site (IRES) sequences of viral origin allows dicistronic mRNAs to be translated efficiently (Oh and Sarnow, *Current Opinion in Genetics and Development* 3:295–300, 1993; Ramesh et al., *Nucleic Acids Research* 24:2697–2700, 1996). Expression of a heterologous cDNA as part of a dicistronic mRNA followed by the gene for a selectable marker (e.g. DHFR) has been shown to improve transfectability of the host and expression of the heterologous cDNA (Kaufman, *Meth. in Enzymology*, 1990). Exemplary expression vectors that employ dicistronic mRNAs are pTR-DC/GFP described by Mosser et al., *Biotechniques* 22:150–161, 1997, and p2A5I described by Morris et al., *Animal Cell Technology*, 1997, pp. 529–534.

A useful high expression vector, pCAVNOT, has been described by Mosley et al., *Cell* 59:335–348, 1989. Other expression vectors for use in mammalian host cells can be constructed as disclosed by Okayama and Berg (*Mol. Cell Biol.* 3:280, 1983). A useful system for stable high level expression of mammalian cDNAs in C127 murine mammary epithelial cells can be constructed substantially as described by Cosman et al. (*Mol. Immunol.* 23:935, 1986). A useful high expression vector, PMLSV N1/N4, described by Cosman et al., *Nature* 312:768, 1984, has been deposited as ATCC 39890. Additional useful mammalian expression vectors are described in EP-A-0367566, and in WO 91/18982, incorporated by reference herein. In yet another alternative, the vectors can be derived from retroviruses.

Additional useful expression vectors, pFLAG® and pDC311, can also be used. FLAG® technology is centered on the fusion of a low molecular weight (1 kD), hydrophilic, FLAG® marker peptide to the N-terminus of a recombinant protein expressed by pFLAG® expression vectors. pDC311 is another specialized vector used for expressing proteins in CHO cells. pDC311 is characterized by a bicistronic sequence containing the gene of interest and a dihydrofolate reductase (DHFR) gene with an internal ribosome binding site for DHFR translation, an expression augmenting sequence element (EASE), the human CMV promoter, a tripartite leader sequence, and a polyadenylation site.

Regarding signal peptides that may be employed, the native signal peptide may be replaced by a heterologous signal peptide or leader sequence, if desired. The choice of signal peptide or leader may depend on factors such as the type of host cells in which the recombinant polypeptide is to be produced. To illustrate, examples of heterologous signal peptides that are functional in mammalian host cells include the signal sequence for interleukin-7 (IL-7) described in U.S. Pat. No. 4,965,195; the signal sequence for interleukin-2 receptor described in Cosman et al., *Nature* 312:768 (1984); the interleukin4 receptor signal peptide described in EP 367,566; the type I interleukin-1 receptor signal peptide described in U.S. Pat. No. 4,968,607; and the type II interleukin-1 receptor signal peptide described in EP 460,846.

Purification

The invention also includes methods of isolating and purifying the polypeptides and fragments thereof.

Isolation and Purification

The "isolated" polypeptides or fragments thereof encompassed by this invention are polypeptides or fragments that are not in an environment identical to an environment in which it or they can be found in nature. The "purified" polypeptides or fragments thereof encompassed by this invention are essentially free of association with other proteins or polypeptides, for example, as a purification product of recombinant expression systems such as those described above or as a purified product from a non-recombinant source such as naturally occurring cells and/or tissues.

In one preferred embodiment, the purification of recombinant polypeptides or fragments can be accomplished using fusions of polypeptides or fragments of the invention to another polypeptide to aid in the purification of polypeptides or fragments of the invention. Such fusion partners can include the poly-His or other antigenic identification peptides described above as well as the Fc moieties described previously.

With respect to any type of host cell, as is known to the skilled artisan, procedures for purifying a recombinant polypeptide or fragment will vary according to such factors as the type of host cells employed and whether or not the recombinant polypeptide or fragment is secreted into the culture medium.

In general, the recombinant polypeptide or fragment can be isolated from the host cells if not secreted, or from the medium or supernatant if soluble and secreted, followed by one or more concentration, salting-out, ion exchange, hydrophobic interaction, affinity purification or size exclusion chromatography steps. As to specific ways to accomplish these steps, the culture medium first can be concentrated using a commercially available protein concentration filter, for example, an Amicon or Millipore Pellicon ultrafiltration unit. Following the concentration step, the concentrate can be applied to a purification matrix such as a gel filtration medium. Alternatively, an anion exchange resin can be employed, for example, a matrix or substrate having pendant diethylaminoethyl (DEAE) groups. The matrices can be acrylamide, agarose, dextran, cellulose or other types commonly employed in protein purification. Alternatively, a cation exchange step can be employed. Suitable cation exchangers include various insoluble matrices comprising sulfopropyl or carboxymethyl groups. In addition, a chromatofocusing step can be employed. Alternatively, a hydrophobic interaction chromatography step can be employed. Suitable matrices can be phenyl or octyl moieties bound to resins. In addition, affinity chromatography with a matrix which selectively binds the recombinant protein can be employed. Examples of such resins employed are lectin columns, dye columns, and metal-chelating columns. Finally, one or more reversed-phase high performance liquid chromatography (RP-HPLC) steps employing hydrophobic RP-HPLC media, (e.g., silica gel or polymer resin having pendant methyl, octyl, octyldecyl or other aliphatic groups) can be employed to further purify the polypeptides. Some or all of the foregoing purification steps, in various combinations, are well known and can be employed to provide an isolated and purified recombinant protein.

It is also possible to utilize an affinity column comprising a polypeptide-binding protein of the invention, such as a monoclonal antibody generated against polypeptides of the invention, to affinity-purify expressed polypeptides. These polypeptides can be removed from an affinity column using conventional techniques, e.g., in a high salt elution buffer and then dialyzed into a lower salt buffer for use or by changing pH or other components depending on the affinity matrix utilized, or be competitively removed using the naturally occurring substrate of the affinity moiety, such as a polypeptide derived from the invention.

In this aspect of the invention, polypeptide-binding proteins, such as the anti-polypeptide antibodies of the invention or other proteins that may interact with the polypeptide of the invention, can be bound to a solid phase support such as a column chromatography matrix Adherence of polypeptide-binding proteins of the invention to a solid phase contacting surface can be accomplished by any means, for example, magnetic microspheres can be coated with these polypeptide-binding proteins and held in the incubation vessel through a magnetic field. Suspensions of cell mixtures are contacted with the solid phase that has such polypeptide-binding proteins thereon.

The desired degree of purity depends on the intended use of the protein. A relatively high degree of purity is desired when the polypeptide is to be administered in vivo, for example. In such a case, the polypeptides are purified such that no protein bands corresponding to other proteins are detectable upon analysis by SDS-polyacrylamide gel electrophoresis (SDS-PAGE). It will be recognized by one skilled in the pertinent field that multiple bands corresponding to the polypeptide may be visualized by SDS-PAGE, due to differential glycosylation; differential post-translational processing, and the like. Most preferably, the polypeptide of the invention is purified to substantial homogeneity, as indicated by a single protein band upon analysis by SDS-PAGE. The protein band may be visualized by silver staining, Coomassie blue staining, or (if the protein is radiolabeled) by autoradiography.

Use of DAKAR Nucleic Acid or Oligonucleotides

In addition to being used to express polypeptides as described above, the nucleic acids of the invention, including DNA, and oligonucleotides thereof can be used as probes to identify nucleic acid encoding proteins having kinase activity.

Probes

Among the uses of nucleic acids of the invention is the use of fragments as probes or primers. Such fragments generally comprise at least about 17 contiguous nucleotides of a DNA sequence. In other embodiments, a DNA fragment comprises at least 30, or at least 60, contiguous nucleotides of a DNA sequence.

Because homologs of SEQ ID NO:1 from other mammalian species are contemplated herein, probes based on the murine DNA sequence of SEQ ID NO:1 may be used to screen cDNA libraries derived from other mammalian species, using conventional cross-species hybridization techniques.

Using knowledge of the genetic code in combination with the amino acid sequences set forth above, sets of degenerate oligonucleotides can be prepared. Such oligonucleotides are useful as primers, e.g., in polymerase chain reactions (PCR), whereby DNA fragments are isolated and amplified.

Use of DAKAR Polypeptides and Fragmented Polypeptides

Uses include, but are not limited to, the following:

Purifying proteins and measuring activity thereof

Research Reagents

Molecular weight and Isoelectric focusing markers

Controls for peptide fragmentation

Identification of unknown proteins

Preparation of Antibodies

Purification Reagents

The polypeptides of the invention find use as a protein purification reagent. The polypeptides may be used to purify binding partner proteins such as proteins which interact preferentially through association with the ankyrin repeat domain of DAKAR and proteins which, by virtue of being the natural substrates of DAKAR, bind to its kinase catalytic site.

In particular embodiments, a polypeptide (in any form described herein that is capable of binding a binding partner) is attached to a solid support by conventional procedures. As one example, affinity chromatography columns containing functional groups that will react with functional groups on amino acid side chains of proteins are available (Pharmacia Biotech, Inc., Piscataway, N.J.). In an alternative, a polypeptide/Fc protein (as discussed above) is attached to Protein A- or Protein G-containing chromatography columns through interaction with the Fc moiety.

Measuring Activity

Polypeptides also find use in measuring the biological activity of binding partner proteins in terms of their binding affinity. The polypeptides thus may be employed by those conducting "quality assurance" studies, e.g., to monitor shelf life and stability of protein under different conditions. For example, the polypeptides may be employed in a binding affinity study to measure the biological activity of a binding partner protein that has been stored at different temperatures, or produced in different cell types. The proteins also may be used to determine whether biological activity is retained after modification of a binding partner protein (e.g., chemical modification, truncation, mutation, etc.). The binding affinity of the modified binding partner protein is compared to that of an unmodified binding partner protein to detect any adverse impact of the modifications on biological activity of binding partner. The biological activity of a binding partner protein thus can be ascertained before it is used in a research study, for example.

In particularly preferred embodiments, the isolated DAKAR polypeptide fragments or fusion proteins can be used to assay protein kinase activity.

Research Agents

Another embodiment of the invention is the use of isolated DAKAR polypeptides, fusion proteins, or a fragment thereof containing the isolated protein kinase domain of DAKAR in in vitro or in vivo assays to determine protein kinase activity. A hallmark of protein kinases is their ability to phosphorylate other proteins and to auto-phosphorylate. Therefore, in one aspect of the invention, the isolated polypeptides with kinase activity can be used in assays to phosphorylate target proteins, radiolabel target proteins with $^{32}P$, and identify proteins having phosphatase activity. Exemplary methods of phosphorylation assays set forth above are disclosed in U.S. Pat. No. 5,447,860 which is incorporated herein by reference. In addition to full length polypeptides, the invention also includes the isolated active kinase domains of kinases which can function as reagents in kinase assays.

Kinase assays are typically carried out by combining DAKAR, or an active kinase domain, with radiolabeled ATP ($\gamma^{32}P$-ATP) and a peptide or protein substrate in a buffer solution. The peptide substrates generally range from 8 to 30 amino acids in length or the substrate may also be a protein known to be phosphorylated readily by DAKAR. Many such general kinase substrates are known, e.g. $\alpha$ or $\beta$ casein, histone H1, myelin basic protein, etc. After incubation of this reaction mixture at 20–37° C. for a suitable time, the DAKAR mediated transfer of radioactive phosphate from ATP to the substrate protein or substrate peptide can be determined by methods well known in the art, such as, for example, spotting the radioactive products onto phosphocellulose paper, followed by washing and liquid scintillation counting, gel electrophoresis followed by autoradiography, and scintillation proximity assay.

The purpose of such an assay is to identify substances which interfere with the rate of substrate phosphorylation. Such inhibitory substances could serve as lead compounds in the development of pharmaceuticals for the treatment of autoimmune, inflammatory, infectious or neoplastic diseases in which there is a disregulation of the apoptotic processes mediated by DAKAR. It is conceivable that compounds which inhibit DAKAR could have merit as more general inhibitors of the class of protein kinases which mediate death signaling, including (but not limited to) those mentioned above.

DAKAR, like other kinases, could play a central role in apoptosis which involves cellular signal transduction pathways. As such, alterations in the expression and/or activation of DAKAR can have profound effects on a plethora of cellular processes. Expression of cloned DAKAR, functionally inactive mutants of DAKAR, or the kinase domain can be used to identify the role a particular protein plays in mediating specific signaling events.

Cellular signaling of ten involves a molecular activation cascade, during which a receptor propagates a ligand-receptor mediated signal by specifically activating intracellular kinases which phosphorylate target substrates, ultimately resulting in the activation of the transcription factor NF-κB and other transcriptions factors and kinases. These substrates can themselves be kinases which become activated following phosphorylation. Alternatively, they can be adaptor molecules that facilitate down stream signaling through protein-protein interaction following phosphorylation. Regardless of the nature of the substrate molecule(s), expressed functionally-active versions of DAKAR, for example the DAKAR kinase domain, can be used in assays such as the yeast 2-hybrid assay to identify what substrate(s) were recognized and altered by DAKAR. As such, these novel DAKAR polypeptides can be used as reagents to identify novel molecules involved in signal transduction pathways. In addition, DAKAR and other down-stream molecules involved in the signal transduction pathway can be potential targets for therapeutic compound(s) that interfere with the apoptosis.

Molecular Weight, Isoelectric Point Markers

The polypeptides of the present invention can be subjected to fragmentation into smaller peptides by chemical and enzymatic means, and the peptide fragments so produced can be used in the analysis of other proteins or polypeptides. For example, such peptide fragments can be used as peptide molecular weight markers, peptide isoelectric point markers, or in the analysis of the degree of peptide fragmentation. Thus, the invention also includes these polypeptides and peptide fragments, as well as kits to aid in the determination of the apparent molecular weight and isoelectric point of an unknown protein and kits to assess the degree of fragmentation of an unknown protein.

Although all methods of fragmentation are encompassed by the invention, chemical fragmentation is a preferred embodiment, and includes the use of cyanogen bromide to cleave under neutral or acidic conditions such that specific cleavage occurs at methionine residues (E. Gross, *Methods in Enz.* 11:238–255, 1967). This can further include additional steps, such as a carboxymethylation step to convert cysteine residues to an unreactive species.

Enzymatic fragmentation is another preferred embodiment, and includes the use of a protease such as Asparaginylendo-peptidase, Arginylendo-peptidase, Achromobacter protease I, Trypsin, *Staphlococcus aureus* V8 protease, Endoproteinase Asp-N, or Endoproteinase Lys-C under conventional conditions to result in cleavage at specific amino acid residues. Asparaginylendo-peptidase can cleave specifically on the carboxyl side of the asparagine residues present within the polypeptides of the invention. Arginylendo-peptidase can cleave specifically on the carboxyl side of the arginine residues present within these polypeptides. Achromobacter protease I can cleave specifically on the carboxyl side of the lysine residues present within the polypeptides (Sakiyama and Nakat, U.S. Pat. No. 5,248,599; T. Masaki et al., *Biochim. Biophys. Acta* 660:44–50, 1981; T. Masaki et al., *Biochim. Biophys. Acta* 660:51–55, 1981). Trypsin can cleave specifically on the carboxyl side of the arginine and lysine residues present within polypeptides of the invention. Enzymatic fragmentation may also occur with a protease that cleaves at multiple amino acid residues. For example, *Staphlococcus aureus* V8 protease can cleave specifically on the carboxyl side of the aspartic and glutamic acid residues present within polypeptides (D. W. Cleveland, *J. Biol. Chem.* 3:1102–1106, 1977). Endoproteinase Asp-N can cleave specifically on the amino side of the asparagine residues present within polypeptides. Endoproteinase Lys-C can cleave specifically on the carboxyl side of the lysine residues present within polypeptides of the invention. Other enzymatic and chemical treatments can likewise be used to specifically fragment these polypeptides into a unique set of specific peptides.

Of course, the peptides and fragments of the polypeptides of the invention can also be produced by conventional recombinant processes and synthetic processes well known in the art. With regard to recombinant processes, the polypeptides and peptide fragments encompassed by invention can have variable molecular weights, depending upon the host cell in which they are expressed.

The molecular weight of these polypeptides can also be varied by fusing additional peptide sequences to both the amino and carboxyl terminal ends of polypeptides of the invention. Fusions of additional peptide sequences at the amino and carboxyl terminal ends of polypeptides of the invention can be used to enhance expression of these polypeptides or aid in the purification of the protein. In addition, fusions of additional peptide sequences at the amino and carboxyl terminal ends of polypeptides of the invention will alter some, but usually not all, of the fragmented peptides of the polypeptides generated by enzymatic or chemical treatment. Of course, mutations can be introduced into polypeptides of the invention using routine and known techniques of molecular biology. For example, a mutation can be designed so as to eliminate a site of proteolytic cleavage by a specific enzyme or a site of cleavage by a specific chemically induced fragmentation procedure. The elimination of the site will alter the peptide fingerprint of polypeptides of the invention upon fragmentation with the specific enzyme or chemical procedure.

Because the unique amino acid sequence of each piece specifies a molecular weight, these pieces can thereafter serve as molecular weight markers using such analysis techniques to assist in the determination of the molecular weight of an unknown protein, polypeptides or fragments thereof. The molecular weight markers of the invention serve particularly well as molecular weight markers for the estimation of the apparent molecular weight of proteins that have similar apparent molecular weights and, consequently, allow increased accuracy in the determination of apparent molecular weight of proteins.

When the invention relates to the use of fragmented peptide molecular weight markers, those markers are preferably at least 10 amino acids in size. More preferably, these fragmented peptide molecular weight markers are between 10 and 100 amino acids in size. Even more preferable are fragmented peptide molecular weight markers between 10 and 50 amino acids in size and especially between 10 and 35 amino acids in size. Most preferable are fragmented peptide molecular weight markers between 10 and 20 amino acids in size.

Among the methods for determining molecular weight are sedimentation, gel electrophoresis, chromatography, and mass spectrometry. A particularly preferred embodiment is denaturing polyacrylamide gel electrophoresis (U. K. Laemmli, *Nature* 227:680–685, 1970). Conventionally, the method uses two separate lanes of a gel containing sodium dodecyl sulfate and a concentration of acrylamide between 6–20%. The ability to simultaneously resolve the marker and the sample under identical conditions allows for increased accuracy. It is understood, of course, that many different techniques can be used for the determination of the molecular weight of an unknown protein using polypeptides of the invention, and that this embodiment in no way limits the scope of the invention.

Each unglycosylated polypeptide or fragment thereof has a pI that is intrinsically determined by its unique amino acid sequence (which pI can be estimated by the skilled artisan using any of the computer programs designed to predict pI values currently available, calculated using any well-known amino acid pKa table, or measured empirically). Therefore these polypeptides and fragments thereof can serve as specific markers to assist in the determination of the isoelectric point of an unknown protein, polypeptide, or fragmented peptide using techniques such as isoelectric focusing. These polypeptide or fragmented peptide markers serve particularly well for the estimation of apparent isoelectric points of unknown proteins that have apparent isoelectric points close to that of the polypeptide or fragmented peptide markers of the invention.

The technique of isoelectric focusing can be further combined with other techniques such as gel electrophoresis to simultaneously separate a protein on the basis of molecular weight and charge. The ability to simultaneously resolve these polypeptide or fragmented peptide markers and the unknown protein under identical conditions allows for increased accuracy in the determination of the apparent isoelectric point of the unknown protein. This is of particular interest in techniques, such as two dimensional electrophoresis (T. D. Brock and M. T. Madigan, *Biology of Microorganisms* 76–77 (Prentice Hall, 6d ed. 1991)), where the nature of the procedure dictates that any markers should be resolved simultaneously with the unknown protein. In addition, with such methods, these polypeptides and fragmented peptides thereof can assist in the determination of both the isoelectric point and molecular weight of an unknown protein or fragmented peptide.

Polypeptides and fragmented peptides can be visualized using two different methods that allow a discrimination between the unknown protein and the molecular weight markers. In one embodiment, the polypeptide and fragmented peptide molecular weight markers of the invention can be visualized using antibodies generated against these markers and conventional immunoblotting techniques. This detection is performed under conventional conditions that do not result in the detection of the unknown protein. It is understood that it may not be possible to generate antibodies against all polypeptide fragments of the invention, since small peptides may not contain immunogenic epitopes. It is further understood that not all antibodies will work in this assay; however, those antibodies which are able to bind polypeptides and fragments of the invention can be readily determined using conventional techniques.

The unknown protein is also visualized by using a conventional staining procedure. The molar excess of unknown protein to polypeptide or fragmented peptide molecular weight markers of the invention is such that the conventional staining procedure predominantly detects the unknown protein. The level of these polypeptide or fragmented peptide molecular weight markers is such as to allow little or no detection of these markers by the conventional staining method. The preferred molar excess of unknown protein to polypeptide molecular weight markers of the invention is between 2 and 100,000 fold. More preferably, the preferred molar excess of unknown protein to these polypeptide molecular weight markers is between 10 and 10,000 fold and especially between 100 and 1,000 fold.

It is understood of course that many techniques can be used for the determination and detection of molecular weight and isoelectric point of an unknown protein, polypeptides, and fragmented peptides thereof using these polypeptide molecular weight markers and peptide fragments thereof and that these embodiments in no way limit the scope of the invention.

In another embodiment, the analysis of the progressive fragmentation of the polypeptides of the invention into specific peptides (D. W. Cleveland et al., *J. Biol. Chem.* 252:1102–1106, 1977), such as by altering the time or temperature of the fragmentation reaction, can be used as a control for the extent of cleavage of an unknown protein. For example, cleavage of the same amount of polypeptide and unknown protein under identical conditions can allow for a direct comparison of the extent of fragmentation. Conditions that result in the complete fragmentation of the polypeptide can also result in complete fragmentation of the unknown protein.

As to the specific use of the polypeptides and fragmented peptides of the invention as molecular weight markers, the fragmentation of the polypeptide of SEQ ID NO:2 with cyanogen bromide generates a unique set of fragmented peptide molecular weight markers with the molecular weights shown in Table I. The distribution of methionine residues determines the number of amino acids in each peptide and the unique amino acid composition of each peptide determines its molecular weight.

TABLE I

Cleavage of DAKAR with cyanogen bromide
DAKAR

| Fragment # | Residues | Mol Wt |
|---|---|---|
| 1 | 1—1 | 149.2 |
| 2 | 234—234 | 149.2 |
| 3 | 74–75 | 278.3 |
| 4 | 97–99 | 441.5 |
| 5 | 130–135 | 763.9 |
| 6 | 171–179 | 913.0 |
| 7 | 65–73 | 1090.3 |
| 8 | 76–96 | 2396.9 |
| 9 | 235–262 | 3095.8 |
| 10 | 100–129 | 3395.9 |
| 11 | 136–170 | 3842.5 |
| 12 | 426–479 | 5935.8 |
| 13 | 179–233 | 6419.4 |
| 14 | 480–543 | 7097.9 |
| 15 | 2–64 | 7172.1 |
| 16 | 700–786 | 9228.3 |
| 17 | 544–699 | 16886.3 |
| 18 | 263–425 | 17662.1 |

In addition, the preferred purified polypeptide of the invention (SEQ ID NO:2) has a calculated molecular weight of approximately 86,613 Daltons in the absence of glycosylation, and use thereof allows increased accuracy in the determination of apparent molecular weight of proteins that have apparent molecular weights close to 86,613 Daltons.

Finally, as to the kits that are encompassed by the invention, the constituents of such kits can be varied, but typically contain the polypeptide and fragmented peptide molecular weight markers. Also, such kits can contain the polypeptides wherein a site necessary for fragmentation has been removed. Furthermore, the kits can contain reagents for the specific cleavage of the polypeptide and the unknown protein by chemical or enzymatic cleavage. Kits can further contain antibodies directed against polypeptides or fragments thereof of the invention.

Identification of Unknown Proteins

As set forth above, a polypeptide or peptide fingerprint can be entered into or compared to a database of known proteins to assist in the identification of the unknown protein using mass spectrometry (W. L. Henzel et al., Proc. Natl. Acad. Sci. USA 90:5011–5015, 1993; D. Fenyo et al., Electrophoresis 19:998–1005, 1998). A variety of computer software programs to facilitate these comparisons are accessible via the Internet, such as Protein Prospector (Internet site: prospector.uscf.edu), MultiIdent (Internet site: www.expasy.ch/sprot/multiident.html), PeptideSearch (Internet site:www.mann.embl-heiedelberg.de...deSearch/FR_PeptideSearch Form.html), and ProFound (Internet site:www.chait-sgi.rockefeller.edu/cgi-bin/prot-id-frag.html). These programs allow the user to specify the cleavage agent and the molecular weights of the fragmented peptides within a designated tolerance. The programs compare observed molecular weights to predicted peptide molecular weights derived from sequence databases to assist in determining the identity of the unknown protein.

In addition, a polypeptide or peptide digest can be sequenced using tandem mass spectrometry (MS/MS) and the resulting sequence searched against databases (J. K. Eng, et al., J. Am. Soc. Mass Spec. 5:976–989 (1994); M. Mann and M. Wilm, Anal. Chem. 66:4390–4399 (1994); J. A. Taylor and R. S. Johnson, Rapid Comm. Mass Spec.11:1067–1075 (1997)). Searching programs that can be used in this process exist on the Internet, such as Lutefisk 97 (Internet site: www.lsbc.com:70/Lutefisk97.html), and the Protein Prospector, Peptide Search and ProFound programs described above.

Therefore, adding the sequence of a gene and its predicted protein sequence and peptide fragments to a sequence database can aid in the identification of unknown proteins using mass spectrometry.

Antibodies

Antibodies that are immunoreactive with the polypeptides of the invention are provided herein. Such antibodies specifically bind to the polypeptides via the antigen-binding sites of the antibody (as opposed to non-specific binding). Thus, the polypeptides, fragments, variants, fusion proteins, etc., as set forth above may be employed as "immunogens" in producing antibodies immunoreactive therewith. More specifically, the polypeptides, fragment, variants, fusion proteins, etc. contain antigenic determinants or epitopes that elicit the formation of antibodies.

These antigenic determinants or epitopes can be either linear or conformational (discontinuous). Linear epitopes are composed of a single section of amino acids of the polypeptide, while conformational or discontinuous epitopes are composed of amino acids sections from different regions of the polypeptide chain that are brought into close proximity upon protein folding (C. A. Janeway, Jr. and P. Travers, *Immuno Biology* 3:9 (Garland Publishing Inc., 2nd ed. 1996)). Because folded proteins have complex surfaces, the number of epitopes available is quite numerous; however, due to the conformation of the protein and steric hinderances, the number of antibodies that actually bind to the epitopes is less than the number of available epitopes (C. A. Janeway, Jr. and P. Travers, *Immuno Biology* 2:14 (Garland Publishing Inc., 2nd ed. 1996)). Epitopes may be identified by any of the methods known in the art.

Thus, one aspect of the present invention relates to the antigenic epitopes of the polypeptides of the invention. Such epitopes are useful for raising antibodies, in particular monoclonal antibodies, as described in more detail below. Additionally, epitopes from the polypeptides of the invention can be used as research reagents, in assays, and to purify specific binding antibodies from substances such as polyclonal sera or supernatants from cultured hybridomas. Such epitopes or variants thereof can be produced using techniques well known in the art such as solid-phase synthesis, chemical or enzymatic cleavage of a polypeptide, or using recombinant DNA technology.

As to the antibodies that can be elicited by the epitopes of the polypeptides of the invention, whether the epitopes have been isolated or remain part of the polypeptides, both polyclonal and monoclonal antibodies may be prepared by conventional techniques. See, for example, *Monoclonal Antibodies, Hybridomas: A New Dimension in Biological Analyses,* Kennet et al. (eds.), Plenum Press, New York (1980); and *Antibodies: A Laboratory Manual,* Harlow and Land (eds.), Cold Spring Harbor Laboratory Press, Cold Spring Harbor, N.Y., (1988).

Hybridoma cell lines that produce monoclonal antibodies specific for the polypeptides of the invention are also contemplated herein. Such hybridomas may be produced and identified by conventional techniques. One method for producing such a hybridoma cell line comprises immunizing an animal with a polypeptide; harvesting spleen cells from the immunized animal; fusing said spleen cells to a myeloma cell line, thereby generating hybridoma cells; and identifying a hybridoma cell line that produces a monoclonal antibody that binds the polypeptide. The monoclonal antibodies may be recovered by conventional techniques.

The monoclonal antibodies of the present invention also include chimeric antibodies, e.g., humanized versions of murine monoclonal antibodies. Such humanized antibodies may be prepared by known techniques and offer the advantage of reduced immunogenicity when the antibodies are administered to humans. In one embodiment, a humanized monoclonal antibody comprises the variable region of a murine antibody (or just the antigen binding site thereof) and a constant region derived from a human antibody. Alternatively, a humanized antibody fragment may comprise the antigen binding site of a murine monoclonal antibody and a variable region fragment (lacking the antigen-binding site) derived from a human antibody. Procedures for the production of chimeric and further engineered monoclonal antibodies include those described in Riechmann et al. (*Nature* 332:323, 1988), Liu et al. (*PNAS* 84:3439, 1987), Larrick et al. (*Bio/Technology* 7:934, 1989), and Winter and Harris (*TIPS* 14:139, May, 1993). Procedures to generate antibodies transgenically can be found in GB 2,272,440, U.S. Pat. Nos. 5,569,825 and 5,545,806 and related patents claiming priority therefrom, all of which are incorporated by reference herein.

Antigen-binding fragments of the antibodies, which may be produced by conventional techniques, are also encompassed by the present invention. Examples of such fragments include, but are not limited to, Fab and F(ab')$_2$ fragments. Antibody fragments and derivatives produced by genetic engineering techniques are also provided.

In one embodiment, the antibodies are specific for the polypeptides of the present invention and do not cross-react with other proteins. Screening procedures by which such antibodies may be identified are well known, and may involve immunoaffinity chromatography, for example.

Uses Thereof

The antibodies of the invention can be used in assays to detect the presence of the polypeptides or fragments of the invention, either in vitro or in vivo. The antibodies also may be employed in purifying polypeptides or fragments of the invention by immunoaffinity chromatography.

Those antibodies that additionally can block binding of the polypeptides of the invention to the binding partner(s) may be used to inhibit a biological activity that results from such binding. Such blocking antibodies may be identified using any suitable assay procedure, such as by testing antibodies for the ability to inhibit binding of DAKAR to the binding partner(s). Alternatively, blocking antibodies may be identified in assays for the ability to inhibit a biological effect that results from binding of DAKAR to its binding partner(s).

Such an antibody may be employed in an in vitro procedure, or administered in vivo to inhibit a biological activity mediated by the entity that generated the antibody. Disorders caused or exacerbated (directly or indirectly) by the interaction of DAKAR with a binding partner may be treated. A therapeutic method involves in vivo administration of a blocking antibody to a mammal in an amount effective in inhibiting a DAKAR-mediated biological activity. Monoclonal antibodies are generally preferred for use in such therapeutic methods. In one embodiment, an antigen-binding antibody fragment is employed.

Antibodies may be screened for agonistic (i.e., ligand-mimicking) properties. Such antibodies, upon binding to a DAKAR binding partner(s), induce biological effects (e.g., transduction of biological signals) similar to the biological effects induced when DAKAR binds to a binding partner.

Compositions comprising an antibody that is directed against DAKAR, and a physiologically acceptable diluent, excipient, or carrier, are provided herein. Suitable components of such compositions are as described above for compositions containing DAKAR or DAKAR binding partner proteins.

Also provided herein are conjugates comprising a detectable (e.g., diagnostic) or therapeutic agent, attached to the antibody. Examples of such agents are presented above. The conjugates find use in in vitro or in vivo procedures.

The following examples are provided to further illustrate particular embodiments of the invention, and are not to be construed as limiting the scope of the present invention.

EXAMPLE 1

Isolation of the Nucleic Acid

The original cDNA clone from which the sequence is derived was obtained from the mouse keratinocyte transit amplifying cell library that is maintained by Genesis Research and Development Corporation Limited, Auckland, New Zealand. An independent clone was obtained from the murine thymic stromal cell Z210R.1 library. Confirmation of the position of the initiating methionine was obtained by inspection of a publicly available murine EST having the accession number AI317448.

EXAMPLE 2

Use of DAKAR Polypeptides in an ELISA

Serial dilutions of DAKAR-containing samples (in 50 mM $NaHCO_3$, brought to pH 9 with NaOH) are coated onto Linbro/Titertek 96 well flat bottom E.I.A. microtitration plates (ICN Biomedicals Inc., Aurora, Ohio) at 100:1/well. After incubation at 4° C. for 16 hours, the wells are washed six times with 200:1 PBS containing 0.05% Tween-20 (PBS-Tween). The wells are then incubated with FLAG®-DAKAR binding partner at 1 µg/ml in PBS-Tween with 5% fetal calf serum (FCS) for 90 minutes (100:1 per well), followed by washing as above. Next, each well is incubated with the anti-FLAG® (monoclonal antibody M2 at 1 µg/ml in PBS-Tween containing 5% FCS for 90 minutes (100:1 per well), followed by washing as above. Subsequently, wells are incubated with a polyclonal goat anti-mIgG1-specific horseradish peroxidase-conjugated antibody (a 1:5000 dilution of the commercial stock in PBS-Tween containing 5% FCS) for 90 minutes (100:1 per well). The HRP-conjugated antibody is obtained from Southern Biotechnology Associates, Inc., Birmingham, Ala. Wells then are washed six times, as above.

For development of the ELISA, a substrate mix [100:1 per well of a 1:1 premix of the TMB Peroxidase Substrate and Peroxidase Solution B (Kirkegaard Perry Laboratories, Gaithersburg, Md.)] is added to the wells. After sufficient color reaction, the enzymatic reaction is terminated by addition of 2 N $H_2SO_4$ (50:1 per well). Color intensity (indicating DAKAR-binding activity) is determined by measuring extinction at 450 nm on a V Max plate reader (Molecular Devices, Sunnyvale, Calif.).

EXAMPLE 3

Monoclonal Antibodies That Bind

This example illustrates a method for preparing monoclonal antibodies that bind DAKAR polypeptides. Suitable immunogens that may be employed in generating such antibodies include, but are not limited to, purified DAKAR polypeptide or an immunogenic fragment thereof, or fusion proteins containing DAKAR (e.g., a soluble DAKAR/Fc fusion protein).

Purified DAKAR can be used to generate monoclonal antibodies immunoreactive therewith, using conventional techniques such as those described in U.S. Pat. No. 4,411,993. Briefly, mice are immunized with DAKAR immunogen emulsified in complete Freund's adjuvant, and injected in amounts ranging from 10–100 :g subcutaneously or intraperitoneally. Ten to twelve days later, the immunized animals are boosted with additional DAKAR emulsified in incomplete Freund's adjuvant. Mice are periodically boosted thereafter on a weekly to bi-weekly immunization schedule. Serum samples are periodically taken by retro-orbital bleeding or tail-tip excision to test for DAKAR antibodies by dot blot assay, ELISA (Enzyme-Linked Immunosorbent Assay) or inhibition of DAKAR-binding partner binding or inhibition of kinase catalytic activity.

Following detection of an appropriate antibody titer, positive animals are provided one last intravenous injection of DAKAR in saline. Three to four days later, the animals are sacrificed, spleen cells harvested, and spleen cells are fused to a murine myeloma cell line, e.g., NS1 or preferably P3x63Ag8.653 (ATCC CRL 1580). Fusions generate hybridoma cells, which are plated in multiple microtiter plates in a HAT (hypoxanthine, aminopterin and thymidine) selective medium to inhibit proliferation of non-fused cells, myeloma hybrids, and spleen cell hybrids.

The hybridoma cells are screened by ELISA for reactivity against purified DAKAR by adaptations of the techniques disclosed in Engvall et al., *Immunochem.* 8:871, 1971 and in U.S. Pat. No. 4,703,004. A preferred screening technique is the antibody capture technique described in Beckmann et al., (*J. Immunol.* 144:4212, 1990) Positive hybridoma cells can be injected intraperitoneally into syngeneic BALB/c mice to produce ascites containing high concentrations of anti-DAKAR monoclonal antibodies. Alternatively, hybridoma cells can be grown in vitro in flasks or roller bottles by various techniques. Monoclonal antibodies produced in mouse ascites can be purified by ammonium sulfate precipitation, followed by gel exclusion chromatography. Alternatively, affinity chromatography based upon binding of antibody to Protein A or Protein G can also be used, as can affinity chromatography based upon binding to DAKAR.

EXAMPLE 4

Northern Blot Analysis

The tissue distribution of DAKAR mRNA can be investigated by Northern blot analysis, as follows. An aliquot of a radiolabeled probe ($^{32}$P-labeled PCR product derived from sequence contained within the DAKAR open reading frame) is added to both human and murine multiple tissue Northern blots (Clontech, Palo Alto, Calif.; Biochain, Palo Alto, Calif.). Hybridization is conducted as recommended by the manufacturer and using Clontechs ExpressHyb hybridization solution. The post hybridization wash protocol is also as described by the manufacturer.

Using the protocol described above, it was determined that a single transcript of approximately 4.0 kilobases (kb) was present in murine liver and kidney and to a lesser extent in lung and testis. A similar sized transcript was also detected in human kidney and pancreas and to a lesser extent in fetal liver, liver, lung and placenta.

EXAMPLE 5

Measuring Kinase Activity of DAKAR

Isolated DAKAR polypeptide or fusion proteins containing the isolated protein kinase domain of DAKAR can be used in an assay of protein kinase activity. Typically this would be carried out by combining DAKAR with radiolabeled ATP ($\gamma^{32}$P-ATP) and a magnesium salt in buffer solution containing a peptide or protein substrate. The peptide substrates are generally from 8–30 amino acids in length and may terminate at the N- or C-terminus with three or more lysine or arginine residues to facilitate binding of the peptide to phosphocellulose paper. The substrate may also be a protein known to be phosphorylated readily by DAKAR. Many such general kinase substrates are known, such as, α or β casein, histone H1, myelin basic protein, etc. After incubation of this reaction mixture at 20–37° C. for a suitable time, the transfer of radioactive phosphate from ATP to the substrate protein or substrate peptide may be monitored, by spotting of the reaction mixture onto phosphocellulose paper, and subsequent washing of the paper with a dilute solution of phosphoric acid, in the case of a peptide substrate, or by application of the reaction products to a gel electrophoresis system followed by autoradiographic detection in the case of proteins. Other methods are available to conveniently measure the DAKAR-mediated transfer of phosphate to substrate proteins, such as the scintillation proximity assay, these methods are well known to those practiced in the art.

The specification is most thoroughly understood in light of the teachings of the references cited within the specification which are hereby incorporated by reference. The embodiments within the specification provide an illustration of embodiments of the invention and should not be construed to limit the scope of the invention. The skilled artisan readily recognizes that many other embodiments are encompassed by the invention.

What is claimed is:

1. A method for determining the kinase activity of an isolated polypeptide comprising combining the polypeptide with a substrate and detecting the phosphorylation of the substrate, wherein the polypeptide comprises an amino acid sequence selected from the group consisting of:
   (a) SEQ ID NO:2;
   (b) amino acids 1–786 of SEQ ID NO:2;
   (c) amino acids 17–297 of SEQ ID NO:2;
   (d) the amino acid sequence of a fragment of a kinase domain of at least 20 amino acids, the amino acid sequence of said kinase domain extending from amino acid 17 to amino acid 297 of SEQ ID NO:2, wherein said fragment has kinase activity; and
   (e) the amino acid sequence of a polypeptide produced by a method comprising culturing a host cell in a suitable culture medium, wherein the host cell comprises a recombinant vector comprising a nucleic acid encoding said polypeptide and selected from the group consisting of:
      (e1) an isolated nucleic acid encoding an amino acid sequence comprising the sequence of SEQ ID NO:2;
      (e2) an isolated nucleic acid encoding amino acids 1–786 of SEQ ID NO:2;
      (e3) an isolated nucleic acid encoding amino acids 17–297 of SEQ ID NO:2; and
      (e4) an isolated nucleic acid encoding the amino acid sequence of a fragment of a kinase domain of at least 20 amino acids, the amino acid sequence of said kinase domain extending from amino acid 17 to amino acid 297 of SEQ ID NO:2, wherein the fragment has kinase activity.

2. The method of claim 1 wherein the substrate is a peptide between 8 and 30 amino acids in length.

3. The method of claim 1 wherein the substrate is selected from the group consisting of alpha casein, beta casein, histone H1, and myelin basic protein.

4. The method of claim 1 wherein the polypeptide and substrate are further combined with radiolabeled ATP.

5. The method of claim 1 wherein the substrate is phosphorylated with $^{32}$P.

6. The method of claim 1 further comprising incubation of the polypeptide and substrate combination at a temperature between 20 and 37 degrees C.

7. The method of claim 1 wherein the polypeptide and substrate are further combined with a potential inhibitor of the activity of the polypeptide.

8. A method for determining the kinase activity of an isolated polypeptide comprising combining the polypeptide with a substrate and a potential inhibitor of the activity of the polypeptide, and detecting the phosphorylation of the substrate by the polypeptide in the presence of said inhibitor, wherein the polypeptide comprises an amino acid sequence selected from the group consisting of:
   (a) SEQ ID NO:2;
   (b) amino acids 1–786 of SEQ ID NO:2; and
   (c) amino acids 17–297 of SEQ ID NO:2.

9. The method of claim 8 wherein the substrate is a peptide between 8 and 30 amino acids in length.

10. The method of claim 8 wherein the substrate is selected from the group consisting of alpha casein, beta casein, histone H1, and myelin basic protein.

11. The method of claim 8 wherein the polypeptide and substrate are further combined with radiolabeled ATP.

12. The method of claim 8 wherein the substrate is phosphorylated with $^{32}$P.

* * * * *

UNITED STATES PATENT AND TRADEMARK OFFICE
CERTIFICATE OF CORRECTION

PATENT NO. : 6,489,130 B1
DATED : December 3, 2002
INVENTOR(S) : Timothy A. Bird and G. Duke Virca It is certified that error appears in the above-identified patent and that said Letters Patent is hereby corrected as shown below:

Column 2,
Line 15, "linase" should read -- kinase --

Column 13,
Line 42, "of ten" should read -- often --

Column 14,
Line 51, "Gin" should read -- Gln --
Line 52, "Gin Ala Ala Phe Ser Gin" should read -- Gln Ala Ala Phe Ser Gln --
Line 56, "Gin" should read -- Gln --

Column 16,
Lines 56-57, "of ten" should read -- often --
Line 58, "(AR S)" should read -- (ARS) --

Column 17,
Line 15, "of ten" should read -- often --
Line 52, "199 1)." should read -- 1991). --

Column 22,
Line 53, "of ten" should read -- often --

Signed and Sealed this

Twenty-ninth Day of April, 2003

JAMES E. ROGAN
*Director of the United States Patent and Trademark Office*

SEQUENCE LISTING

<160> NUMBER OF SEQ ID NOS: 5

<210> SEQ ID NO 1
<211> LENGTH: 2370
<212> TYPE: DNA
<213> ORGANISM: Mus sp.

<400> SEQUENCE: 1

```
ggatccaaag tggagggcga gggccggggc cggtgggctc tggggctgct gcgcaccttc        60
gacgccggcg aattcgcagg ctgggagaag gtgggctcgg gcggcttcgg gcaggtgtac       120
aaggtgcgcc atgtgcactg gaagacgtgg ctcgcgatca agtgctcgcc cagtctgcac       180
gtcgacgaca gggaacgaat ggagctcctg gaggaagcta agaagatgga gatggccaag       240
ttccgataca ttctacctgt gtacggcata tgccaggaac ctgtcggctt ggtcatggag       300
tacatggaga caggctccct ggagaagctg ctggcctcag agccattgcc ttgggacctg       360
cgctttcgca tcgtgcacga gacagccgtg ggcatgaact tcctgcattg catgtctccg       420
ccactgctgc acctagacct gaagccagcg aacatcctgc tggatgccca ctaccatgtc       480
aagatttctg actttgggct ggccaagtgc aatggcatgt cccactctca tgacctcagc       540
atggatggcc tgtttggtac aatcgcttac ctccctccag agcgaattcg tgagaagagc       600
cgcttgtttg acaccaaaca tgatgtatac agcttcgcca ttgtgatctg gggtgtgctt       660
acacagaaga agccatttgc agatgaaaag aacatcctac acatcatgat gaaagtggta       720
aagggccacc gcccagagct gccacccatc tgcagacccc ggccgcgtgc ctgtgccagc       780 ctgataggc tcatgcaacg gtgctggcat gcagaccac aggtgcggcc caccttccaa        840
gaaattacct ctgaaacaga agacctttgt gagaagcctg atgaggaggt gaaagacctg       900
gctcatgagc caggcgagaa aagctctcta gagtccaaga gtgaggccag gcccgagtcc       960
tcacgcctca agcgcgcctc tgctcccccc ttcgataacg actgcagtct ctccgagttg      1020
ctgtcacagt tggactctgg gatctcccag actcttgaag gccccgaaga gctcagccga      1080
agttcctctg aatgcaagct cccatcgtcc agcagtggca agaggctctc gggggtgtcc      1140
tcagtggact cagccttttc ctccagagga tcgctgtcac tgtcttttga gcgggaagct      1200
tcaacaggcg acctgggccc cacagacatc cagaagaaga agctagtgga tgccatcata      1260
```

-continued

```
tcaggggaca ccagcaggct gatgaagatc ctacagcccc aagatgtgga cttggttcta      1320
gacagcagtg ccagcctgct gcacctggct gtggaggccg acaggagga gtgtgtcaag      1380 tggctgctgc ttaacaatgc caaccccaac ctgaccaaca ggaagggctc tacaccactg      1440
catatggctg tggagcggaa gggacgtgga attgtggagc tactgctagc ccggaagacc      1500
agtgtcaatg ccaaggatga agaccagtgg actgccctgc actttgcagc ccagaatggg      1560
gatgaggcca gcacaaggct gctgctagag aagaatgctt ctgtcaatga ggtggacttt      1620
gagggccgaa cacccatgca tgtagcctgc agcatggac aggagaacat tgtgcgcacc       1680
ctgctccgcc gtggtgtgga tgtgggcctg cagggaaagg atgcctggtt gcctctgcac      1740
tatgctgcct ggcagggcca ccttcccatt gttaagctgc tagccaagca gcctggggtg      1800
agtgtgaatg cccagacact agacgggagg acacccctgc acctggctgc tcagaggggg      1860
cattaccgtg tggctcgcat tctcattgac ctgtgctctg atgttaacat ctgcagccta      1920
caggcacaga cacctctgca tgttgctgca gagactggac acactagtac tgccaggcta      1980
ctcttgcatc gtggtgctgg caaggaggct ttgacctcag agggctatac tgccttgcac      2040
ctggcagccc agaatggaca cctggctact gtcaagctgc tcatagagga gaaggctgat      2100
gtgatggctc ggggtcccct gaatcagaca gcactgcacc tggctgctgc ccgtggacac      2160
tcagaggtgg tagaagagct ggtcagtgct gacctcattg acctgtctga tgagcagggc      2220
ctcagcgcac tgcacctggc tgctcagggc aggcattcac agactgtgga cactgctc       2280 aaacatggag cacacatcaa cttgcagagt ctcaagttcc aaggaggcca gagctctgct      2340
gccacgttgc tccgacgcag caagacctag                                       2370
```

<210> SEQ ID NO 2
<211> LENGTH: 786
<212> TYPE: PRT
<213> ORGANISM: Mus sp.

<400> SEQUENCE: 2

```
Met Glu Gly Glu Gly Arg Gly Arg Trp Ala Leu Gly Leu Leu Arg Thr
 1               5                  10                  15

Phe Asp Ala Gly Glu Phe Ala Gly Trp Glu Lys Val Gly Ser Gly Gly
                20                  25                  30

Phe Gly Gln Val Tyr Lys Val Arg His Val His Trp Lys Thr Trp Leu
            35                  40                  45

Ala Ile Lys Cys Ser Pro Ser Leu His Val Asp Asp Arg Glu Arg Met
        50                  55                  60

Glu Leu Leu Glu Glu Ala Lys Lys Met Glu Met Ala Lys Phe Arg Tyr
65                  70                  75                  80

Ile Leu Pro Val Tyr Gly Ile Cys Gln Glu Pro Val Gly Leu Val Met
                85                  90                  95

Glu Tyr Met Glu Thr Gly Ser Leu Glu Lys Leu Leu Ala Ser Glu Pro
            100                 105                 110

Leu Pro Trp Asp Leu Arg Phe Arg Ile Val His Glu Thr Ala Val Gly
        115                 120                 125

Met Asn Phe Leu His Cys Met Ser Pro Leu Leu His Leu Asp Leu
    130                 135                 140

Lys Pro Ala Asn Ile Leu Leu Asp Ala His Tyr His Val Lys Ile Ser
145                 150                 155                 160

Asp Phe Gly Leu Ala Lys Cys Asn Gly Met Ser His Ser His Asp Leu
                165                 170                 175
```

-continued

```
Ser Met Asp Gly Leu Phe Gly Thr Ile Ala Tyr Leu Pro Pro Glu Arg
                180                 185                 190
Ile Arg Glu Lys Ser Arg Leu Phe Asp Thr Lys His Asp Val Tyr Ser
            195                 200                 205
Phe Ala Ile Val Ile Trp Gly Val Leu Thr Gln Lys Lys Pro Phe Ala
        210                 215                 220
Asp Glu Lys Asn Ile Leu His Ile Met Met Lys Val Val Lys Gly His
225                 230                 235                 240
Arg Pro Glu Leu Pro Pro Ile Cys Arg Pro Arg Pro Arg Ala Cys Ala
                245                 250                 255
Ser Leu Ile Gly Leu Met Gln Arg Cys Trp His Ala Asp Pro Gln Val
            260                 265                 270
Arg Pro Thr Phe Gln Glu Ile Thr Ser Glu Thr Glu Asp Leu Cys Glu
        275                 280                 285
Lys Pro Asp Glu Glu Val Lys Asp Leu Ala His Glu Pro Gly Glu Lys
290                 295                 300
Ser Ser Leu Glu Ser Lys Ser Glu Ala Arg Pro Glu Ser Ser Arg Leu
305                 310                 315                 320
Lys Arg Ala Ser Ala Pro Pro Phe Asp Asn Asp Cys Ser Leu Ser Glu
                325                 330                 335
Leu Leu Ser Gln Leu Asp Ser Gly Ile Ser Gln Thr Leu Glu Gly Pro
            340                 345                 350
Glu Glu Leu Ser Arg Ser Ser Glu Cys Lys Leu Pro Ser Ser Ser
        355                 360                 365
Ser Gly Lys Arg Leu Ser Gly Val Ser Ser Val Asp Ser Ala Phe Ser
370                 375                 380
Ser Arg Gly Ser Leu Ser Leu Ser Phe Glu Arg Glu Ala Ser Thr Gly
385                 390                 395                 400
Asp Leu Gly Pro Thr Asp Ile Gln Lys Lys Lys Leu Val Asp Ala Ile
                405                 410                 415
Ile Ser Gly Asp Thr Ser Arg Leu Met Lys Ile Leu Gln Pro Gln Asp
            420                 425                 430
Val Asp Leu Val Leu Asp Ser Ala Ser Leu Leu His Leu Ala Val
        435                 440                 445
Glu Ala Gly Gln Glu Glu Cys Val Lys Trp Leu Leu Asn Asn Ala
        450                 455                 460
Asn Pro Asn Leu Thr Asn Arg Lys Gly Ser Thr Pro Leu His Met Ala
465                 470                 475                 480
Val Glu Arg Lys Gly Arg Gly Ile Val Glu Leu Leu Ala Arg
                485                 490                 495
Thr Ser Val Asn Ala Lys Asp Glu Asp Gln Trp Thr Ala Leu His Phe
            500                 505                 510
Ala Ala Gln Asn Gly Asp Glu Ala Ser Thr Arg Leu Leu Leu Glu Lys
        515                 520                 525
Asn Ala Ser Val Asn Glu Val Asp Phe Glu Gly Arg Thr Pro Met His
        530                 535                 540
Val Ala Cys Gln His Gly Gln Glu Asn Ile Val Arg Thr Leu Leu Arg
545                 550                 555                 560
Arg Gly Val Asp Val Gly Leu Gln Gly Lys Asp Ala Trp Leu Pro Leu
                565                 570                 575
His Tyr Ala Ala Trp Gln Gly His Leu Pro Ile Val Lys Leu Leu Ala
            580                 585                 590
Lys Gln Pro Gly Val Ser Val Asn Ala Gln Thr Leu Asp Gly Arg Thr
```

-continued

```
                595                 600                 605

Pro Leu His Leu Ala Ala Gln Arg Gly His Tyr Arg Val Ala Arg Ile
            610                 615                 620

Leu Ile Asp Leu Cys Ser Asp Val Asn Ile Cys Ser Leu Gln Ala Gln
625                 630                 635                 640

Thr Pro Leu His Val Ala Ala Glu Thr Gly His Thr Ser Thr Ala Arg
                645                 650                 655

Leu Leu Leu His Arg Gly Ala Gly Lys Glu Ala Leu Thr Ser Glu Gly
            660                 665                 670

Tyr Thr Ala Leu His Leu Ala Ala Gln Asn Gly His Leu Ala Thr Val
675                 680                 685

Lys Leu Leu Ile Glu Glu Lys Ala Asp Val Met Ala Arg Gly Pro Leu
            690                 695                 700

Asn Gln Thr Ala Leu His Leu Ala Ala Arg Gly His Ser Glu Val
705                 710                 715                 720

Val Glu Glu Leu Val Ser Ala Asp Leu Ile Asp Leu Ser Asp Glu Gln
                725                 730                 735

Gly Leu Ser Ala Leu His Leu Ala Ala Gln Gly Arg His Ser Gln Thr
            740                 745                 750

Val Glu Thr Leu Leu Lys His Gly Ala His Ile Asn Leu Gln Ser Leu
755                 760                 765

Lys Phe Gln Gly Gly Gln Ser Ser Ala Ala Thr Leu Leu Arg Arg Ser
            770                 775                 780

Lys Thr
785
```

<210> SEQ ID NO 3
<211> LENGTH: 8
<212> TYPE: PRT
<213> ORGANISM: Artificial
<220> FEATURE:
<223> OTHER INFORMATION: FLAG peptide

<400> SEQUENCE: 3

```
Asp Tyr Lys Asp Asp Asp Asp Lys
1               5
```

<210> SEQ ID NO 4
<211> LENGTH: 27
<212> TYPE: PRT
<213> ORGANISM: Artificial
<220> FEATURE:
<223> OTHER INFORMATION: Leucine zipper derived from lung surfactant
      protein D (SPD)

<400> SEQUENCE: 4

```
Pro Asp Val Ala Ser Leu Arg Gln Gln Val Glu Ala Leu Gln Gly Gln
1               5                   10                  15

Val Gln His Leu Gln Ala Ala Phe Ser Gln Tyr
            20                  25
```

<210> SEQ ID NO 5
<211> LENGTH: 33
<212> TYPE: PRT
<213> ORGANISM: Artificial
<220> FEATURE:
<223> OTHER INFORMATION: Leucine zipper peptide

```
-continued

<400> SEQUENCE: 5

Arg Met Lys Gln Ile Glu Asp Lys Ile Glu Ile Leu Ser Lys Ile
1               5                   10                  15

Tyr His Ile Glu Asn Glu Ile Ala Arg Ile Lys Lys Leu Ile Gly Glu
            20                  25                  30

Arg
```